(12) United States Patent
Feldman et al.

(10) Patent No.: US 8,219,174 B2
(45) Date of Patent: Jul. 10, 2012

(54) METHOD OF CALIBRATING AN ANALYTE-MEASUREMENT DEVICE, AND ASSOCIATED METHODS, DEVICES AND SYSTEMS

(75) Inventors: Benjamin J. Feldman, Oakland, CA (US); Geoffrey V. McGarraugh, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 391 days.

(21) Appl. No.: 12/494,197

(22) Filed: Jun. 29, 2009

(65) Prior Publication Data
US 2009/0265129 A1    Oct. 22, 2009

Related U.S. Application Data

(63) Continuation of application No. 11/929,149, filed on Oct. 30, 2007, now Pat. No. 8,116,840, which is a continuation of application No. 10/975,207, filed on Oct. 27, 2004, now Pat. No. 7,299,082.

(60) Provisional application No. 60/516,599, filed on Oct. 31, 2003.

(51) Int. Cl.
 *A61B 5/05* (2006.01)
 *A61B 5/00* (2006.01)
(52) U.S. Cl. .................. 600/345; 600/347; 600/365
(58) Field of Classification Search .................. 600/309, 600/345–366
See application file for complete search history.

(56) References Cited

U.S. PATENT DOCUMENTS

| | | |
|---|---|---|
| 3,164,534 A | 1/1965 | Free |
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |

(Continued)

FOREIGN PATENT DOCUMENTS

DE    150656    9/1981

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Navin Natnithithadha
(74) *Attorney, Agent, or Firm* — Jackson & Co., LLP

(57) ABSTRACT

The invention relates to a method for calibrating an analyte-measurement device that is used to evaluate a concentration of analyte in bodily fluid at or from a measurement site in a body. The method involves measuring a concentration, or calibration concentration, of an analyte in blood from an "off-finger" calibration site, and calibrating the analyte-measurement device based on that calibration concentration. The invention also relates to a device, system, or kit for measuring a concentration of an analyte in a body, which employs a calibration device for adjusting analyte concentration measured in bodily fluid based on an analyte concentration measured in blood from an "off-finger" calibration site.

20 Claims, 8 Drawing Sheets

U.S. PATENT DOCUMENTS

| | | |
|---|---|---|
| 4,392,849 A | 7/1983 | Petre et al. |
| 4,425,920 A | 1/1984 | Bourland et al. |
| 4,431,004 A | 2/1984 | Bessman et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,550,076 A | 10/1985 | Chikazawa et al. |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,820,399 A | 4/1989 | Senda et al. |
| 4,854,322 A | 8/1989 | Ash et al. |
| 4,871,351 A | 10/1989 | Feingold |
| 4,890,620 A | 1/1990 | Gough |
| 4,891,104 A | 1/1990 | Liston et al. |
| 4,897,162 A | 1/1990 | Lewandowski et al. |
| 4,925,268 A | 5/1990 | Iyer et al. |
| 4,953,552 A | 9/1990 | DeMarzo |
| 4,974,929 A | 12/1990 | Curry |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,200,051 A | 4/1993 | Cozzette et al. |
| 5,202,261 A * | 4/1993 | Musho et al. ............ 204/403.09 |
| 5,202,317 A | 4/1993 | Bruice |
| 5,210,778 A | 5/1993 | Massart |
| 5,217,966 A | 6/1993 | Bruice |
| 5,227,405 A | 7/1993 | Friedovich et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,645 A | 10/1995 | Albery et al. |
| 5,466,575 A | 11/1995 | Cozzette et al. |
| 5,468,562 A | 11/1995 | Farivar et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,610,293 A | 3/1997 | Riley et al. |
| 5,628,310 A | 5/1997 | Rao et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,665,222 A | 9/1997 | Heller et al. |
| 5,696,109 A | 12/1997 | Malfroy-Camine et al. |
| 5,711,001 A | 1/1998 | Bussan et al. |
| 5,711,861 A | 1/1998 | Ward et al. |
| 5,733,259 A | 3/1998 | Valcke et al. |
| 5,771,890 A | 6/1998 | Tamada |
| 5,772,586 A | 6/1998 | Heinonen et al. |
| 5,791,344 A | 8/1998 | Schulman et al. |
| 5,882,494 A | 3/1999 | Van Antwerp |
| 5,899,855 A | 5/1999 | Brown |
| 5,906,921 A | 5/1999 | Ikeda et al. |
| 5,914,026 A | 6/1999 | Blubaugh et al. |
| 5,925,021 A | 7/1999 | Castellano et al. |
| 5,935,224 A | 8/1999 | Svancarek et al. |
| 5,942,979 A | 8/1999 | Luppino |
| 5,947,957 A | 9/1999 | Morris |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,994,339 A | 11/1999 | Crapo et al. |
| 5,995,860 A | 11/1999 | Sun et al. |
| 6,001,067 A | 12/1999 | Shults et al. |
| 6,011,077 A | 1/2000 | Muller |
| 6,023,629 A | 2/2000 | Tamada |
| 6,024,699 A | 2/2000 | Surwit et al. |
| 6,049,727 A | 4/2000 | Crothall |
| 6,081,736 A | 6/2000 | Colvin et al. |
| 6,083,710 A | 7/2000 | Heller et al. |
| 6,084,093 A | 7/2000 | Riley et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,103,714 A | 8/2000 | Fridovich et al. |
| 6,110,155 A | 8/2000 | Baudino |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,122,536 A | 9/2000 | Sun et al. |
| 6,127,356 A | 10/2000 | Crapo et al. |
| 6,134,461 A | 10/2000 | Say et al. |
| 6,143,164 A | 11/2000 | Heller et al. |
| 6,144,869 A | 11/2000 | Berner et al. |
| 6,162,611 A | 12/2000 | Heller et al. |
| 6,175,752 B1 | 1/2001 | Say et al. |
| 6,190,315 B1 | 2/2001 | Kost et al. |
| 6,200,265 B1 | 3/2001 | Walsh et al. |
| 6,212,416 B1 | 4/2001 | Ward et al. |
| 6,214,817 B1 | 4/2001 | Riley et al. |
| 6,219,574 B1 | 4/2001 | Cormier et al. |
| 6,233,471 B1 | 5/2001 | Berner et al. |
| 6,245,758 B1 | 6/2001 | Stern et al. |
| 6,248,067 B1 | 6/2001 | Causey, III et al. |
| 6,254,586 B1 | 7/2001 | Mann et al. |
| 6,267,002 B1 | 7/2001 | Ehwald et al. |
| 6,268,161 B1 | 7/2001 | Han et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,298,254 B2 | 10/2001 | Tamada |
| 6,299,347 B1 | 10/2001 | Pompei |
| 6,306,104 B1 | 10/2001 | Cunningham et al. |

| Patent No. | Date | Inventors |
|---|---|---|
| 6,309,884 B1 | 10/2001 | Cooper et al. |
| 6,329,161 B1 | 12/2001 | Heller et al. |
| 6,338,790 B1 | 1/2002 | Feldman et al. |
| 6,343,225 B1 | 1/2002 | Clark, Jr. |
| 6,360,888 B1 | 3/2002 | McIvor et al. |
| 6,366,794 B1 | 4/2002 | Moussy et al. |
| 6,368,274 B1 | 4/2002 | Van Antwerp et al. |
| 6,372,045 B1 | 4/2002 | McCabe et al. |
| 6,377,828 B1 | 4/2002 | Chaiken et al. |
| 6,379,301 B1 | 4/2002 | Worthington et al. |
| 6,400,974 B1 | 6/2002 | Lesho |
| 6,403,788 B1 | 6/2002 | Meunier et al. |
| 6,424,847 B1 | 7/2002 | Mastrototaro et al. |
| 6,427,088 B1 | 7/2002 | Bowman, IV et al. |
| 6,434,409 B1 | 8/2002 | Pfeiffer et al. |
| 6,436,255 B2 | 8/2002 | Yamamoto et al. |
| 6,438,414 B1 | 8/2002 | Conn et al. |
| 6,440,068 B1 | 8/2002 | Brown et al. |
| 6,448,239 B1 | 9/2002 | Groves et al. |
| 6,466,810 B1 | 10/2002 | Ward et al. |
| 6,475,181 B1 | 11/2002 | Potter et al. |
| 6,475,196 B1 | 11/2002 | Vachon |
| 6,477,395 B2 | 11/2002 | Schulman et al. |
| 6,477,891 B2 | 11/2002 | Ehwald et al. |
| 6,478,736 B1 | 11/2002 | Mault |
| 6,479,477 B1 | 11/2002 | Crapo et al. |
| 6,484,046 B1 | 11/2002 | Say et al. |
| 6,491,657 B2 | 12/2002 | Rowe et al. |
| 6,497,729 B1 | 12/2002 | Moussy et al. |
| 6,508,785 B1 | 1/2003 | Eppstein |
| 6,512,939 B1 | 1/2003 | Colvin et al. |
| 6,514,718 B2 | 2/2003 | Heller et al. |
| 6,525,041 B1 | 2/2003 | Neumann et al. |
| 6,530,915 B1 | 3/2003 | Eppstein et al. |
| 6,541,490 B1 | 4/2003 | Campbell et al. |
| 6,544,212 B2 | 4/2003 | Galley et al. |
| 6,544,975 B1 | 4/2003 | Crapo et al. |
| 6,551,494 B1 | 4/2003 | Feldman et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,573,257 B2 | 6/2003 | Malfroy-Camine et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,948 B1 | 7/2003 | Malfroy-Camine et al. |
| 6,591,125 B1 | 7/2003 | Buse et al. |
| 6,591,126 B2 | 7/2003 | Roeper et al. |
| 6,592,746 B1 | 7/2003 | Schmid-Schoenbein et al. |
| 6,595,919 B2 | 7/2003 | Berner et al. |
| 6,599,407 B2 | 7/2003 | Taniike et al. |
| 6,602,678 B2 | 8/2003 | Kwon et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,620,123 B1 | 9/2003 | Mitragotri et al. |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,679,841 B2 | 1/2004 | Bojan et al. |
| 6,685,699 B1 | 2/2004 | Eppstein et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,723,077 B2 | 4/2004 | Pickup et al. |
| 6,733,446 B2 | 5/2004 | Lebel et al. |
| 6,740,075 B2 | 5/2004 | Lebel et al. |
| 6,740,215 B1 | 5/2004 | Nakaminami et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,770,729 B2 | 8/2004 | Van Antwerp |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,835,387 B2 | 12/2004 | Herrmann |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,885,196 B2 | 4/2005 | Taniike et al. |
| 6,892,085 B2 | 5/2005 | McIvor et al. |
| 6,895,263 B2 | 5/2005 | Shin et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,029,444 B2 | 4/2006 | Shin et al. |
| 7,041,068 B2 | 5/2006 | Freeman et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,153,265 B2 * | 12/2006 | Vachon ........................ 600/365 |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,267,665 B2 | 9/2007 | Steil et al. |
| 7,276,029 B2 | 10/2007 | Goode et al. |
| 7,299,082 B2 | 11/2007 | Feldman et al. |
| 7,310,544 B2 | 12/2007 | Brister et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode et al. |

| Patent/Pub No. | Date | Inventors |
|---|---|---|
| 7,591,801 B2 | 9/2009 | Brauker et al. |
| 7,599,726 B2 | 10/2009 | Goode et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,699,694 B2 | 4/2010 | Hill |
| 7,711,402 B2 | 5/2010 | Shults et al. |
| 7,713,574 B2 | 5/2010 | Brister et al. |
| 7,715,893 B2 | 5/2010 | Kamath et al. |
| 2001/0020125 A1 | 9/2001 | Kurnik et al. |
| 2001/0039393 A1 | 11/2001 | Mori et al. |
| 2001/0041830 A1 | 11/2001 | Varalli et al. |
| 2002/0006634 A1 | 1/2002 | Han et al. |
| 2002/0019022 A1 | 2/2002 | Dunn et al. |
| 2002/0023852 A1 | 2/2002 | Mcivor et al. |
| 2002/0026110 A1 | 2/2002 | Parris et al. |
| 2002/0042090 A1 | 4/2002 | Heller et al. |
| 2002/0042407 A1 | 4/2002 | Fridovich et al. |
| 2002/0068860 A1 | 6/2002 | Clark |
| 2002/0082490 A1 | 6/2002 | Roeper et al. |
| 2002/0082543 A1 | 6/2002 | Park et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2002/0169635 A1 | 11/2002 | Shillingburg |
| 2002/0183604 A1 | 12/2002 | Gowda et al. |
| 2003/0004403 A1 | 1/2003 | Drinan et al. |
| 2003/0023317 A1 | 1/2003 | Brauker et al. |
| 2003/0031699 A1 | 2/2003 | Van Antwerp |
| 2003/0032874 A1 | 2/2003 | Rhodes et al. |
| 2003/0042137 A1 | 3/2003 | Mao et al. |
| 2003/0045798 A1 | 3/2003 | Hular et al. |
| 2003/0055032 A1 | 3/2003 | Groves et al. |
| 2003/0065254 A1 | 4/2003 | Schulman et al. |
| 2003/0065308 A1 | 4/2003 | Lebel et al. |
| 2003/0069281 A1 | 4/2003 | Fridovich et al. |
| 2003/0077702 A1 | 4/2003 | Shah et al. |
| 2003/0077772 A1 | 4/2003 | Shah et al. |
| 2003/0078560 A1 | 4/2003 | Miller et al. |
| 2003/0099682 A1 | 5/2003 | Moussy et al. |
| 2003/0100821 A1 | 5/2003 | Heller et al. |
| 2003/0118577 A1 | 6/2003 | Weill et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0190341 A1 | 10/2003 | Shalaby et al. |
| 2003/0199790 A1 | 10/2003 | Boecker et al. |
| 2003/0199837 A1 | 10/2003 | Vachon |
| 2003/0208113 A1 | 11/2003 | Mault et al. |
| 2003/0212317 A1 | 11/2003 | Kovatchev et al. |
| 2003/0212346 A1 | 11/2003 | Yuzhakov et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0028612 A1 | 2/2004 | Singaram et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0063167 A1 | 4/2004 | Kaastrup et al. |
| 2004/0064068 A1 | 4/2004 | DeNuzzio et al. |
| 2004/0064133 A1 | 4/2004 | Miller et al. |
| 2004/0074785 A1 | 4/2004 | Holker et al. |
| 2004/0106858 A1 | 6/2004 | Say et al. |
| 2004/0110722 A1 | 6/2004 | Ornberg et al. |
| 2004/0116332 A1 | 6/2004 | Ornberg et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0267300 A1 | 12/2004 | Mace |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0054909 A1 | 3/2005 | Petisce et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0215871 A1 | 9/2005 | Feldman et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister |

| | | | | | |
|---|---|---|---|---|---|
| 2006/0155180 A1 | 7/2006 | Brister et al. | 2008/0214915 A1 | 9/2008 | Brister et al. |
| 2006/0166629 A1 | 7/2006 | Reggiardo | 2008/0214918 A1 | 9/2008 | Brister et al. |
| 2006/0173260 A1 | 8/2006 | Gaoni et al. | 2008/0228051 A1 | 9/2008 | Shults et al. |
| 2006/0173406 A1 | 8/2006 | Hayes et al. | 2008/0228054 A1 | 9/2008 | Shults et al. |
| 2006/0173444 A1 | 8/2006 | Choy et al. | 2008/0242961 A1 | 10/2008 | Brister et al. |
| 2006/0183985 A1 | 8/2006 | Brister et al. | 2008/0255434 A1 | 10/2008 | Hayter et al. |
| 2006/0189863 A1 | 8/2006 | Peyser et al. | 2008/0255437 A1 | 10/2008 | Hayter |
| 2006/0219576 A1 | 10/2006 | Jina et al. | 2008/0255808 A1 | 10/2008 | Hayter |
| 2006/0222566 A1 | 10/2006 | Brauker et al. | 2008/0256048 A1 | 10/2008 | Hayter |
| 2006/0224109 A1 | 10/2006 | Steil et al. | 2008/0262469 A1 | 10/2008 | Brister et al. |
| 2006/0229512 A1 | 10/2006 | Petisce et al. | 2008/0275313 A1 | 11/2008 | Brister et al. |
| 2006/0247508 A1 | 11/2006 | Fennell | 2008/0287761 A1 | 11/2008 | Hayter |
| 2006/0258929 A1 | 11/2006 | Goode et al. | 2008/0287762 A1 | 11/2008 | Hayter |
| 2006/0272652 A1 | 12/2006 | Stocker et al. | 2008/0287763 A1 | 11/2008 | Hayter |
| 2007/0016381 A1 | 1/2007 | Kamath et al. | 2008/0287764 A1 | 11/2008 | Rasdal et al. |
| 2007/0027381 A1 | 2/2007 | Stafford | 2008/0287765 A1 | 11/2008 | Rasdal et al. |
| 2007/0033074 A1 | 2/2007 | Nitzan et al. | 2008/0287766 A1 | 11/2008 | Rasdal et al. |
| 2007/0060814 A1 | 3/2007 | Stafford | 2008/0288180 A1 | 11/2008 | Hayter |
| 2007/0066873 A1 | 3/2007 | Kamath et al. | 2008/0288204 A1 | 11/2008 | Hayter et al. |
| 2007/0071681 A1 | 3/2007 | Gadkar et al. | 2008/0296155 A1 | 12/2008 | Shults et al. |
| 2007/0073129 A1 | 3/2007 | Shah et al. | 2008/0306368 A1 | 12/2008 | Goode et al. |
| 2007/0078320 A1 | 4/2007 | Stafford | 2008/0306434 A1 | 12/2008 | Dobbles et al. |
| 2007/0078321 A1 | 4/2007 | Mazza et al. | 2008/0306435 A1 | 12/2008 | Kamath et al. |
| 2007/0078322 A1 | 4/2007 | Stafford | 2008/0306444 A1 | 12/2008 | Brister et al. |
| 2007/0078323 A1 | 4/2007 | Reggiardo et al. | 2008/0312841 A1 | 12/2008 | Hayter |
| 2007/0106135 A1 | 5/2007 | Sloan et al. | 2008/0312842 A1 | 12/2008 | Hayter |
| 2007/0124002 A1 | 5/2007 | Estes et al. | 2008/0312844 A1 | 12/2008 | Hayter et al. |
| 2007/0149875 A1 | 6/2007 | Ouyang et al. | 2008/0312845 A1 | 12/2008 | Hayter et al. |
| 2007/0163880 A1 | 7/2007 | Woo et al. | 2009/0005665 A1 | 1/2009 | Hayter et al. |
| 2007/0168224 A1 | 7/2007 | Letzt et al. | 2009/0006034 A1 | 1/2009 | Hayter et al. |
| 2007/0173706 A1 | 7/2007 | Neinast et al. | 2009/0012379 A1 | 1/2009 | Goode et al. |
| 2007/0173761 A1 | 7/2007 | Kanderian et al. | 2009/0018424 A1 | 1/2009 | Kamath et al. |
| 2007/0179349 A1 | 8/2007 | Hoyme et al. | 2009/0018425 A1 | 1/2009 | Ouyang et al. |
| 2007/0179352 A1 | 8/2007 | Randlov et al. | 2009/0030294 A1 | 1/2009 | Petisce et al. |
| 2007/0191701 A1 | 8/2007 | Feldman et al. | 2009/0033482 A1 | 2/2009 | Hayter et al. |
| 2007/0203407 A1 | 8/2007 | Hoss et al. | 2009/0036747 A1 | 2/2009 | Hayter et al. |
| 2007/0203966 A1 | 8/2007 | Brauker et al. | 2009/0036758 A1 | 2/2009 | Brauker et al. |
| 2007/0235331 A1 | 10/2007 | Simpson et al. | 2009/0036760 A1 | 2/2009 | Hayter |
| 2007/0249922 A1 | 10/2007 | Peyser et al. | 2009/0036763 A1 | 2/2009 | Brauker et al. |
| 2008/0009692 A1 | 1/2008 | Stafford | 2009/0043181 A1 | 2/2009 | Brauker et al. |
| 2008/0017522 A1 | 1/2008 | Heller et al. | 2009/0043182 A1 | 2/2009 | Brauker et al. |
| 2008/0021666 A1 | 1/2008 | Goode, Jr. et al. | 2009/0043525 A1 | 2/2009 | Brauker et al. |
| 2008/0029391 A1 | 2/2008 | Mao et al. | 2009/0043541 A1 | 2/2009 | Brauker et al. |
| 2008/0033254 A1 | 2/2008 | Kamath et al. | 2009/0043542 A1 | 2/2009 | Brauker et al. |
| 2008/0039702 A1 | 2/2008 | Hayter et al. | 2009/0045055 A1 | 2/2009 | Rhodes et al. |
| 2008/0045824 A1 | 2/2008 | Tapsak et al. | 2009/0055149 A1 | 2/2009 | Hayter et al. |
| 2008/0058625 A1 | 3/2008 | McGarraugh et al. | 2009/0062633 A1 | 3/2009 | Brauker et al. |
| 2008/0064937 A1 | 3/2008 | McGarraugh et al. | 2009/0062635 A1 | 3/2009 | Brauker et al. |
| 2008/0071156 A1 | 3/2008 | Brister et al. | 2009/0062767 A1 | 3/2009 | VanAntwerp et al. |
| 2008/0071157 A1 | 3/2008 | McGarraugh et al. | 2009/0063402 A1 | 3/2009 | Hayter |
| 2008/0071158 A1 | 3/2008 | McGarraugh et al. | 2009/0076356 A1 | 3/2009 | Simpson et al. |
| 2008/0081977 A1 | 4/2008 | Hayter et al. | 2009/0076360 A1 | 3/2009 | Brister et al. |
| 2008/0083617 A1 | 4/2008 | Simpson et al. | 2009/0076361 A1 | 3/2009 | Kamath et al. |
| 2008/0086042 A1 | 4/2008 | Brister et al. | 2009/0099436 A1 | 4/2009 | Brister et al. |
| 2008/0086044 A1 | 4/2008 | Brister et al. | 2009/0105636 A1 | 4/2009 | Hayter et al. |
| 2008/0086273 A1 | 4/2008 | Shults et al. | 2009/0124877 A1 | 5/2009 | Goode et al. |
| 2008/0097289 A1 | 4/2008 | Steil et al. | 2009/0124878 A1 | 5/2009 | Goode et al. |
| 2008/0108942 A1 | 5/2008 | Brister et al. | 2009/0124879 A1 | 5/2009 | Brister et al. |
| 2008/0154513 A1 | 6/2008 | Kovatchev et al. | 2009/0124964 A1 | 5/2009 | Leach et al. |
| 2008/0167543 A1 | 7/2008 | Say et al. | 2009/0131768 A1 | 5/2009 | Simpson et al. |
| 2008/0172205 A1 | 7/2008 | Breton et al. | 2009/0131769 A1 | 5/2009 | Leach et al. |
| 2008/0183060 A1 | 7/2008 | Steil et al. | 2009/0131776 A1 | 5/2009 | Simpson et al. |
| 2008/0183061 A1 | 7/2008 | Goode et al. | 2009/0131777 A1 | 5/2009 | Simpson et al. |
| 2008/0183399 A1 | 7/2008 | Goode et al. | 2009/0137886 A1 | 5/2009 | Shariati et al. |
| 2008/0188731 A1 | 8/2008 | Brister et al. | 2009/0137887 A1 | 5/2009 | Shariati et al. |
| 2008/0188796 A1 | 8/2008 | Steil et al. | 2009/0143659 A1 | 6/2009 | Li et al. |
| 2008/0189051 A1 | 8/2008 | Goode et al. | 2009/0143660 A1 | 6/2009 | Brister et al. |
| 2008/0194935 A1 | 8/2008 | Brister et al. | 2009/0156919 A1 | 6/2009 | Brister et al. |
| 2008/0194936 A1 | 8/2008 | Goode et al. | 2009/0156924 A1 | 6/2009 | Shariati et al. |
| 2008/0194937 A1 | 8/2008 | Goode et al. | 2009/0163790 A1 | 6/2009 | Brister et al. |
| 2008/0194938 A1 | 8/2008 | Brister et al. | 2009/0163791 A1 | 6/2009 | Brister et al. |
| 2008/0195232 A1 | 8/2008 | Carr-Brendel et al. | 2009/0164190 A1 | 6/2009 | Hayter |
| 2008/0195967 A1 | 8/2008 | Goode et al. | 2009/0164239 A1 | 6/2009 | Hayter et al. |
| 2008/0197024 A1 | 8/2008 | Simpson et al. | 2009/0164251 A1 | 6/2009 | Hayter |
| 2008/0200788 A1 | 8/2008 | Brister et al. | 2009/0178459 A1 | 7/2009 | Li et al. |
| 2008/0200789 A1 | 8/2008 | Brister et al. | 2009/0182217 A1 | 7/2009 | Li et al. |
| 2008/0200791 A1 | 8/2008 | Simpson et al. | 2009/0192366 A1 | 7/2009 | Mensinger et al. |
| 2008/0208025 A1 | 8/2008 | Shults et al. | 2009/0192380 A1 | 7/2009 | Shariati et al. |
| 2008/0208113 A1 | 8/2008 | Damiano et al. | 2009/0192722 A1 | 7/2009 | Shariati et al. |

| | | | |
|---|---|---|---|
| 2009/0192724 A1 | 7/2009 | Brauker et al. | |
| 2009/0192745 A1 | 7/2009 | Kamath et al. | |
| 2009/0192751 A1 | 7/2009 | Kamath et al. | |
| 2009/0198118 A1 | 8/2009 | Hayter et al. | |
| 2009/0203981 A1 | 8/2009 | Brauker et al. | |
| 2009/0204341 A1 | 8/2009 | Brauker et al. | |
| 2009/0216103 A1 | 8/2009 | Brister et al. | |
| 2009/0240120 A1 | 9/2009 | Mensinger et al. | |
| 2009/0240128 A1 | 9/2009 | Mensinger et al. | |
| 2009/0240193 A1 | 9/2009 | Mensinger et al. | |
| 2009/0242399 A1 | 10/2009 | Kamath et al. | |
| 2009/0242425 A1 | 10/2009 | Kamath et al. | |
| 2009/0247855 A1 | 10/2009 | Boock et al. | |
| 2009/0247856 A1 | 10/2009 | Boock et al. | |
| 2009/0287073 A1 | 11/2009 | Boock et al. | |
| 2009/0287074 A1 | 11/2009 | Shults et al. | |
| 2009/0299155 A1 | 12/2009 | Yang et al. | |
| 2009/0299156 A1 | 12/2009 | Simpson et al. | |
| 2009/0299162 A1 | 12/2009 | Brauker et al. | |
| 2009/0299276 A1 | 12/2009 | Brauker et al. | |
| 2010/0010324 A1 | 1/2010 | Brauker et al. | |
| 2010/0010331 A1 | 1/2010 | Brauker et al. | |
| 2010/0010332 A1 | 1/2010 | Brauker et al. | |
| 2010/0016687 A1 | 1/2010 | Brauker et al. | |
| 2010/0016698 A1 | 1/2010 | Rasdal et al. | |
| 2010/0022855 A1 | 1/2010 | Brauker et al. | |
| 2010/0030038 A1 | 2/2010 | Brauker et al. | |
| 2010/0030053 A1 | 2/2010 | Goode, Jr. et al. | |
| 2010/0030484 A1 | 2/2010 | Brauker et al. | |
| 2010/0030485 A1 | 2/2010 | Brauker et al. | |
| 2010/0036215 A1 | 2/2010 | Goode, Jr. et al. | |
| 2010/0036216 A1 | 2/2010 | Goode, Jr. et al. | |
| 2010/0036222 A1 | 2/2010 | Goode, Jr. et al. | |
| 2010/0036223 A1 | 2/2010 | Goode, Jr. et al. | |
| 2010/0036225 A1 | 2/2010 | Goode, Jr. et al. | |
| 2010/0041971 A1 | 2/2010 | Goode, Jr. et al. | |
| 2010/0045465 A1 | 2/2010 | Brauker et al. | |
| 2010/0049024 A1 | 2/2010 | Saint et al. | |
| 2010/0057040 A1 | 3/2010 | Hayter | |
| 2010/0057041 A1 | 3/2010 | Hayter | |
| 2010/0057042 A1 | 3/2010 | Hayter | |
| 2010/0057044 A1 | 3/2010 | Hayter | |
| 2010/0057057 A1 | 3/2010 | Hayter et al. | |
| 2010/0063373 A1 | 3/2010 | Kamath et al. | |
| 2010/0076283 A1 | 3/2010 | Simpson et al. | |
| 2010/0081906 A1 | 4/2010 | Hayter et al. | |
| 2010/0081908 A1 | 4/2010 | Dobbles et al. | |
| 2010/0081910 A1 | 4/2010 | Brister et al. | |
| 2010/0087724 A1 | 4/2010 | Brauker et al. | |
| 2010/0096259 A1 | 4/2010 | Zhang et al. | |
| 2010/0099970 A1 | 4/2010 | Shults et al. | |
| 2010/0099971 A1 | 4/2010 | Shults et al. | |
| 2010/0119693 A1 | 5/2010 | Tapsak et al. | |
| 2010/0121169 A1 | 5/2010 | Petisce et al. | |
| 2010/0168546 A1 | 7/2010 | Kamath et al. | |

FOREIGN PATENT DOCUMENTS

| | | |
|---|---|---|
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1153571 | 11/2001 |
| WO | WO-94/10560 | 5/1994 |
| WO | WO-95/31197 | 11/1995 |
| WO | WO-96/25089 | 8/1996 |
| WO | WO-96/35370 | 11/1996 |
| WO | WO-98/17199 | 4/1998 |
| WO | WO-98/35053 | 8/1998 |
| WO | WO-98/43637 | 10/1998 |
| WO | WO-99/47471 | 9/1999 |
| WO | WO-99/56613 | 11/1999 |
| WO | WO-00/49940 | 8/2000 |
| WO | WO-00/59370 | 10/2000 |
| WO | WO-00/75144 | 12/2000 |
| WO | WO-00/78293 | 12/2000 |
| WO | WO-00/78992 | 12/2000 |
| WO | WO-01/36660 | 5/2001 |
| WO | WO-01/52935 | 7/2001 |
| WO | WO-01/54753 | 8/2001 |
| WO | WO-02/16905 | 2/2002 |
| WO | WO-02/44187 | 6/2002 |
| WO | WO-02/058537 | 8/2002 |
| WO | WO-03/063925 | 8/2003 |
| WO | WO-03/076893 | 9/2003 |
| WO | WO-03/082091 | 10/2003 |
| WO | WO-03/085372 | 10/2003 |
| WO | WO-2004/007756 | 1/2004 |
| WO | WO-2004/028337 | 4/2004 |
| WO | WO-2004/061420 | 7/2004 |
| WO | WO-2005/041766 | 5/2005 |
| WO | WO-2005/078424 | 8/2005 |
| WO | WO-2005/089103 | 9/2005 |
| WO | WO-2006/024671 | 3/2006 |
| WO | WO-2006/079114 | 7/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/043637 | 10/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |

OTHER PUBLICATIONS

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Mediated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Direcnet Study Group, "Accuracy of the GlucoWatch G2 Biographer and the Continuous Glucose Monitoring System During Hyoglycemia," *Diabetes Care*, vol. 27, No. 3, 2004, pp. 722-726.

Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet.

Heller, A., et al., "Amperometric Biosensors Based on Three-Dimensional Hydrogel-Forming Epoxy Networks", *Sensors and Actuators B*, vol. 13-14, 1993, pp. 180-183.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Glucose Measurements Using Blood Extracted from the Forearm and the Finger", TheraSense, Inc., 16 Pages.

McGarraugh, G., et al., "Physiological Influences on Off-Finger Glucose Testing", Diabetes Technology & Therapeutics, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Metzger, M., et al., "Reproducibility of Glucose Measurements Using the Glucose Sensor", *Diabetes Care*, vol. 25, No. 6, 2002, pp. 1185-1191.

Monsod, T. P., et al., "Do Sensor Glucose Levels Accurately Predict Plasma Glucose Concentrations During Hypoglycemia and Hyperinsulinemia?" *Diabetes Care*, vol. 25, No. 5, 2002, pp. 889-893.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", Biosensors, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

U.S. Appl. No. 11/929,149, Office Action received Mar. 22, 2010.
U.S. Appl. No. 10/975,207, Office Action received Aug. 25, 2006.
U.S. Appl. No. 10/975,207, Notice of Allowance received Jul. 13, 2007.
PCT Application No. PCT/US2004/036133, International Search Report and Written Opinion of the International Searching Authority mailed Mar. 4, 2005.
U.S. Appl. No. 11/929,149, Notice of Allowance Nov. 23, 2011.
U.S. Appl. No. 11/929,149, Office Action mailed Aug. 4, 2011.
U.S. Appl. No. 11/929,149, Office Action mailed Jan. 12, 2011.
U.S. Appl. No. 12/421,617, Office Action mailed Oct. 6, 2011.
U.S. Appl. No. 12/494,221, Office Action mailed Oct. 7, 2011.
Canadian Patent Application No. 2,543,962, Notice of Allowance mailed Jun. 6, 2011.

\* cited by examiner

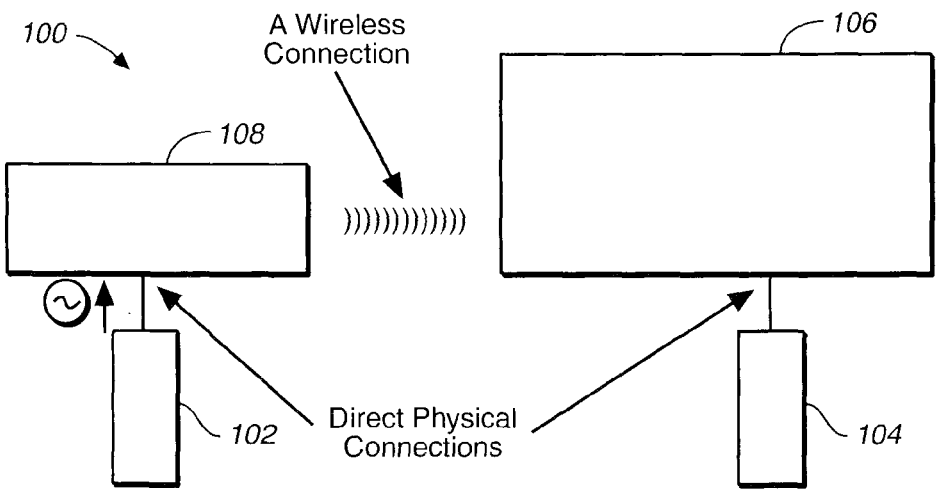
FIG._1A
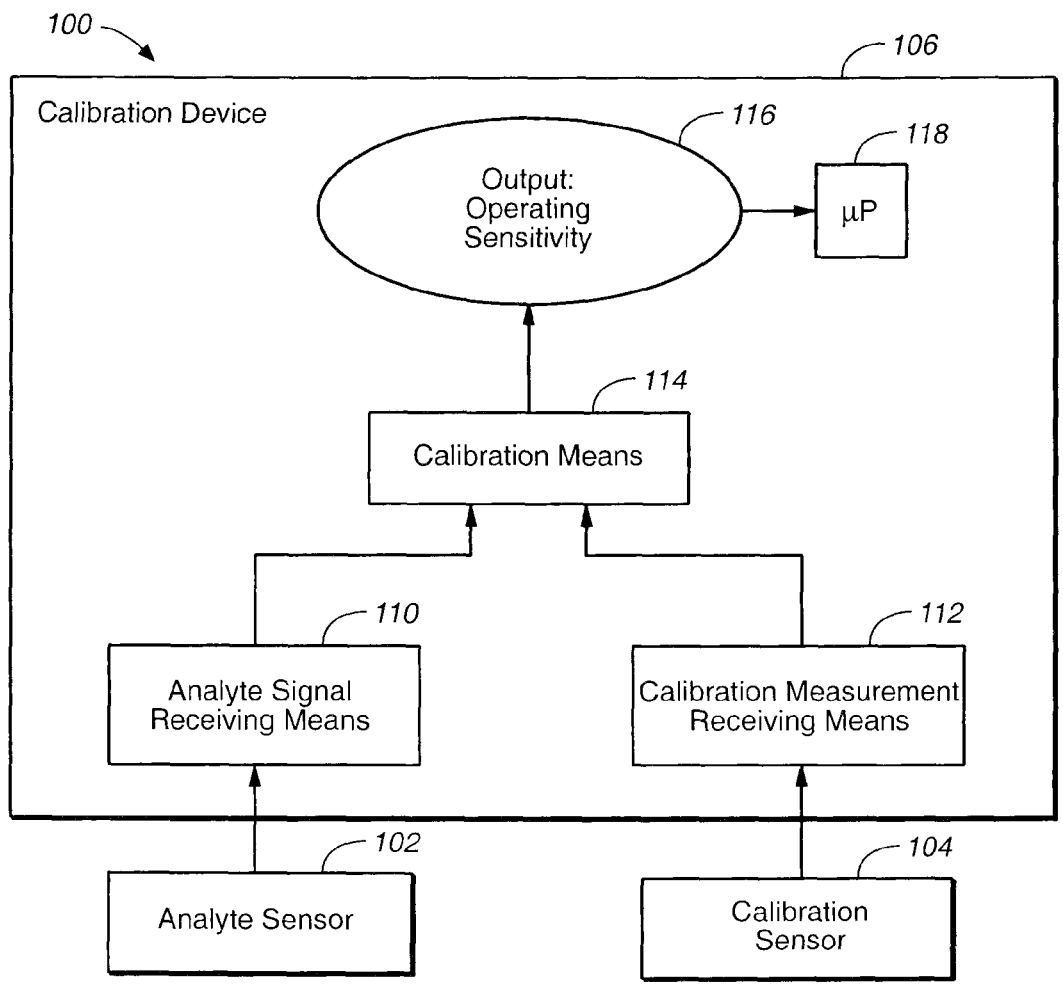
FIG._1B

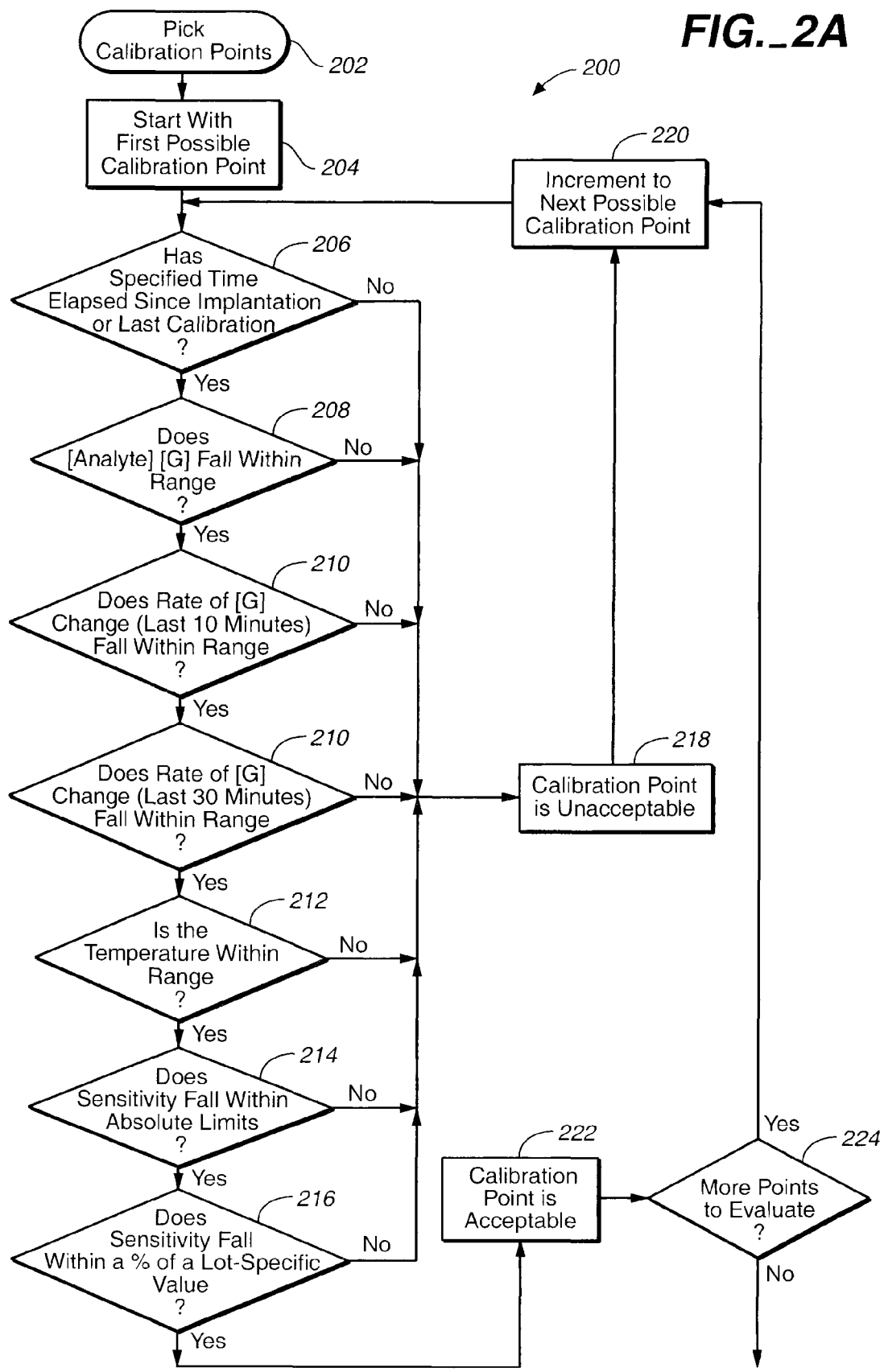
FIG._2A

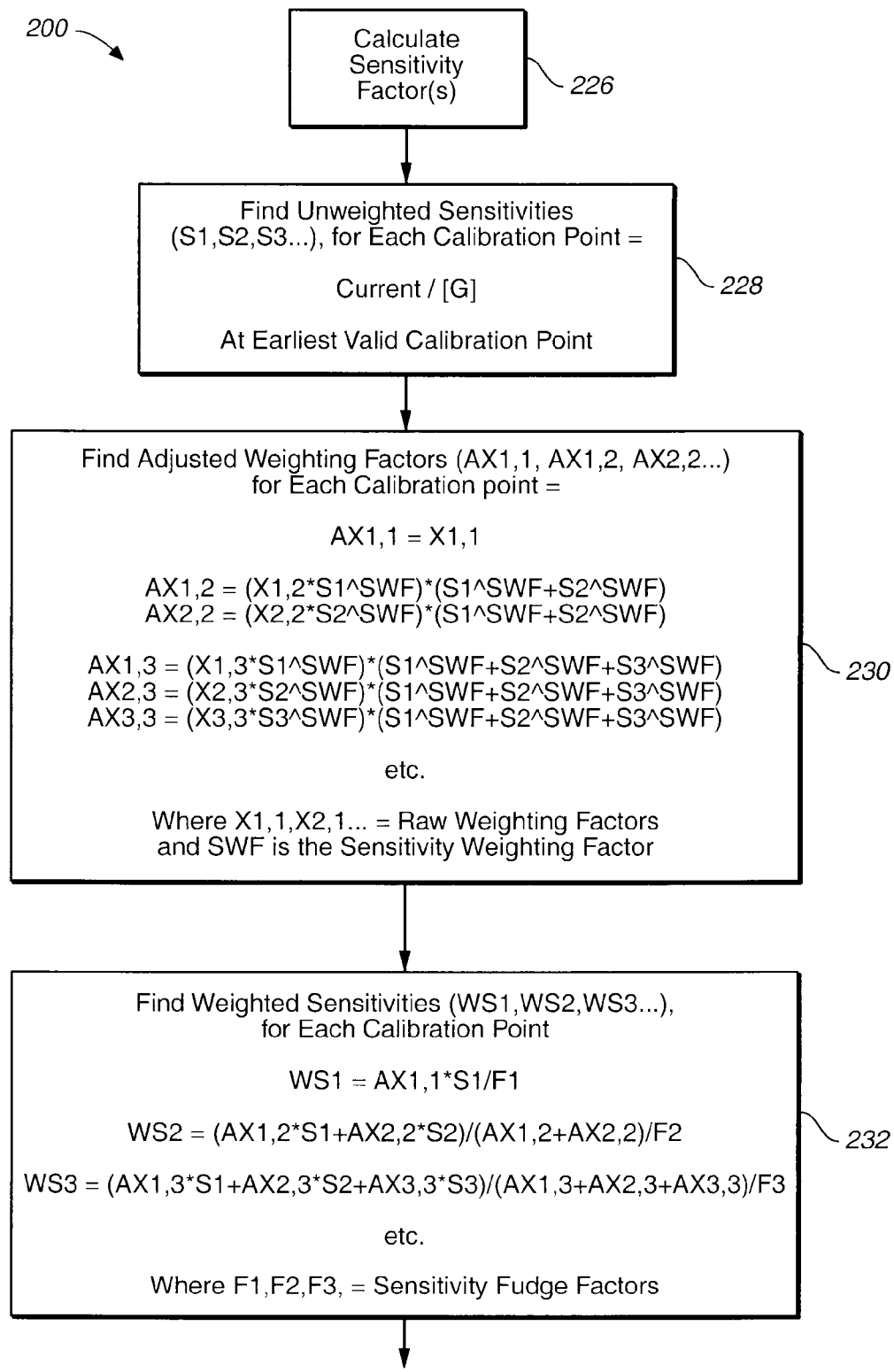
FIG._2B

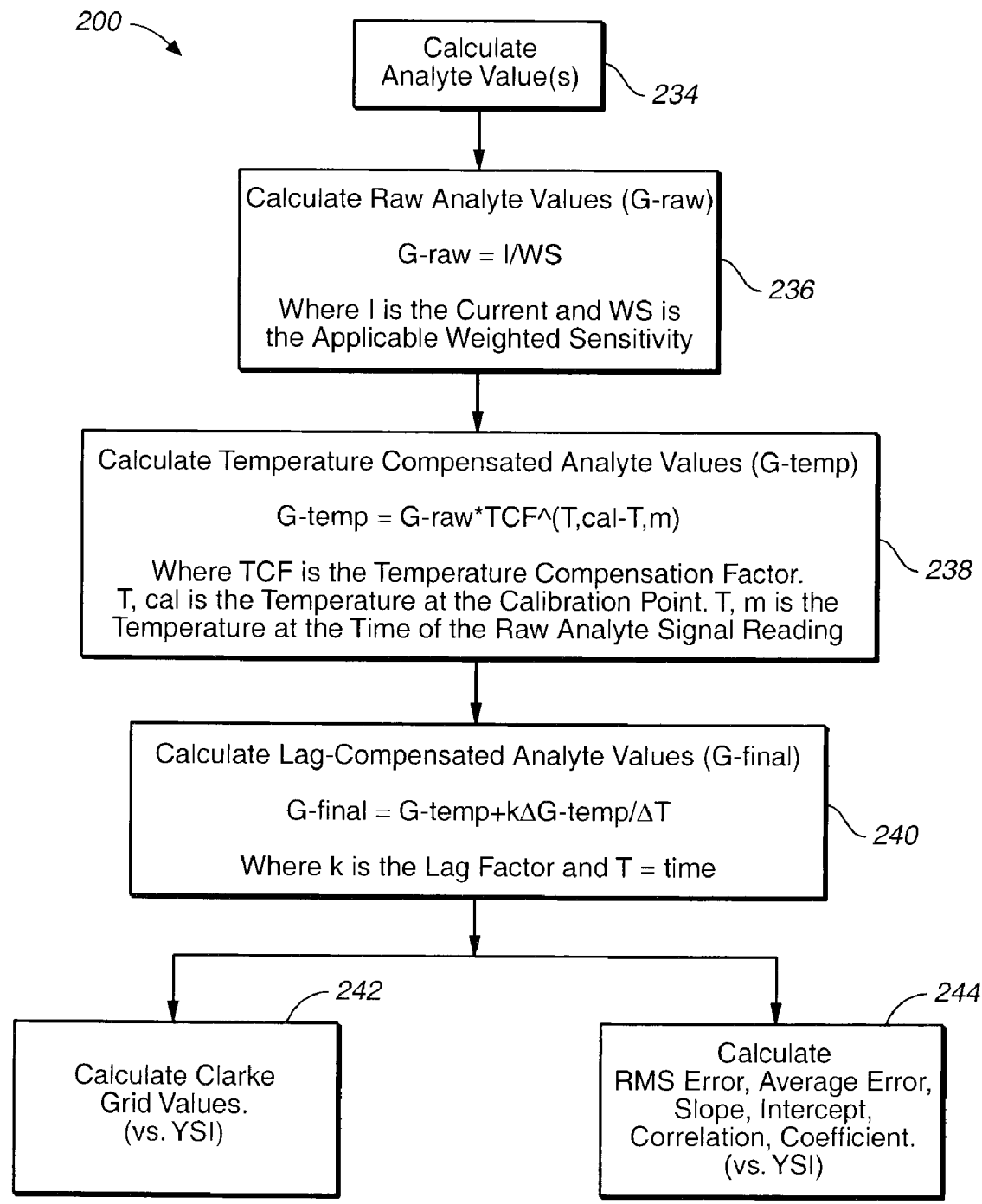
FIG._2C

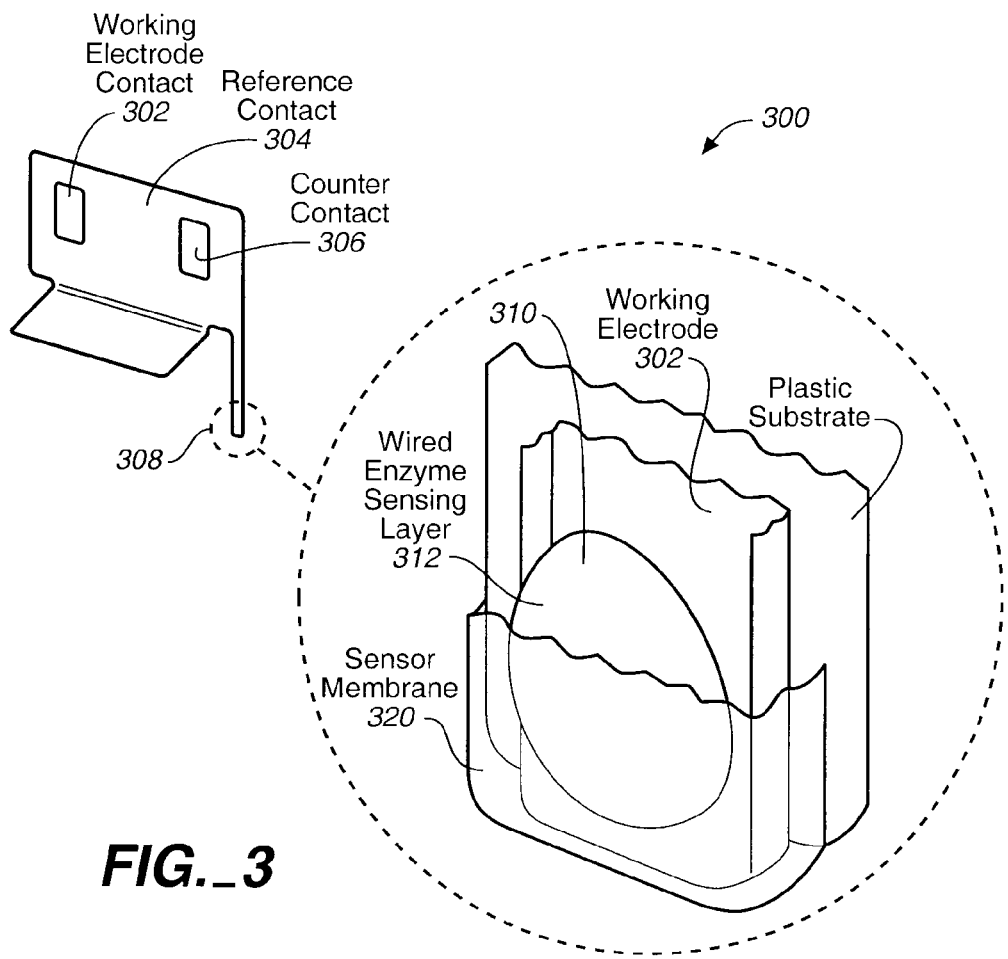
FIG._3
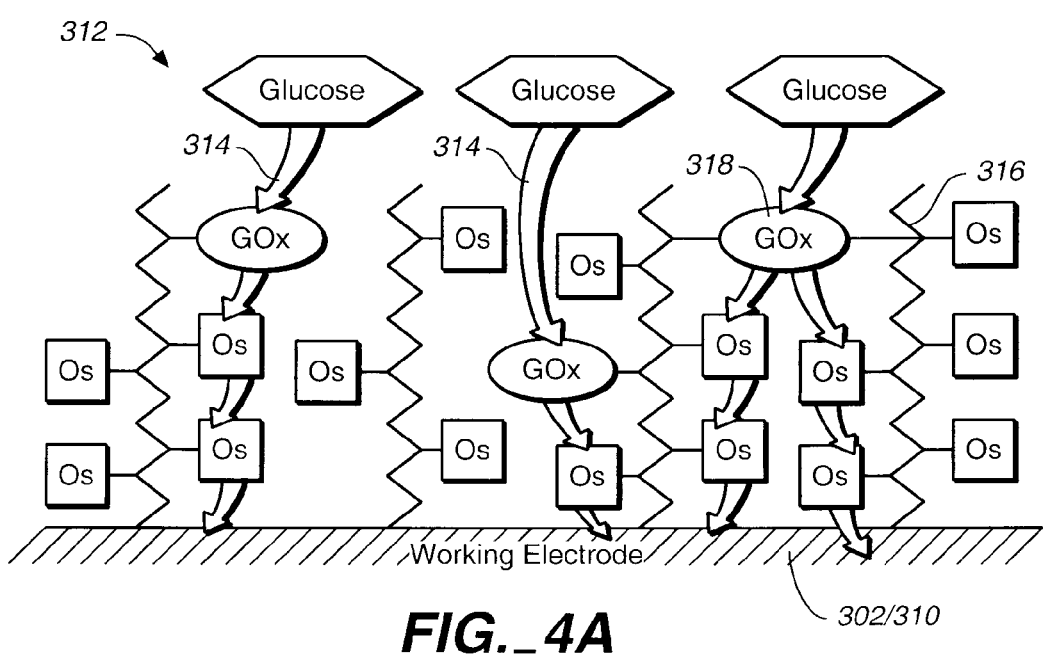
FIG._4A

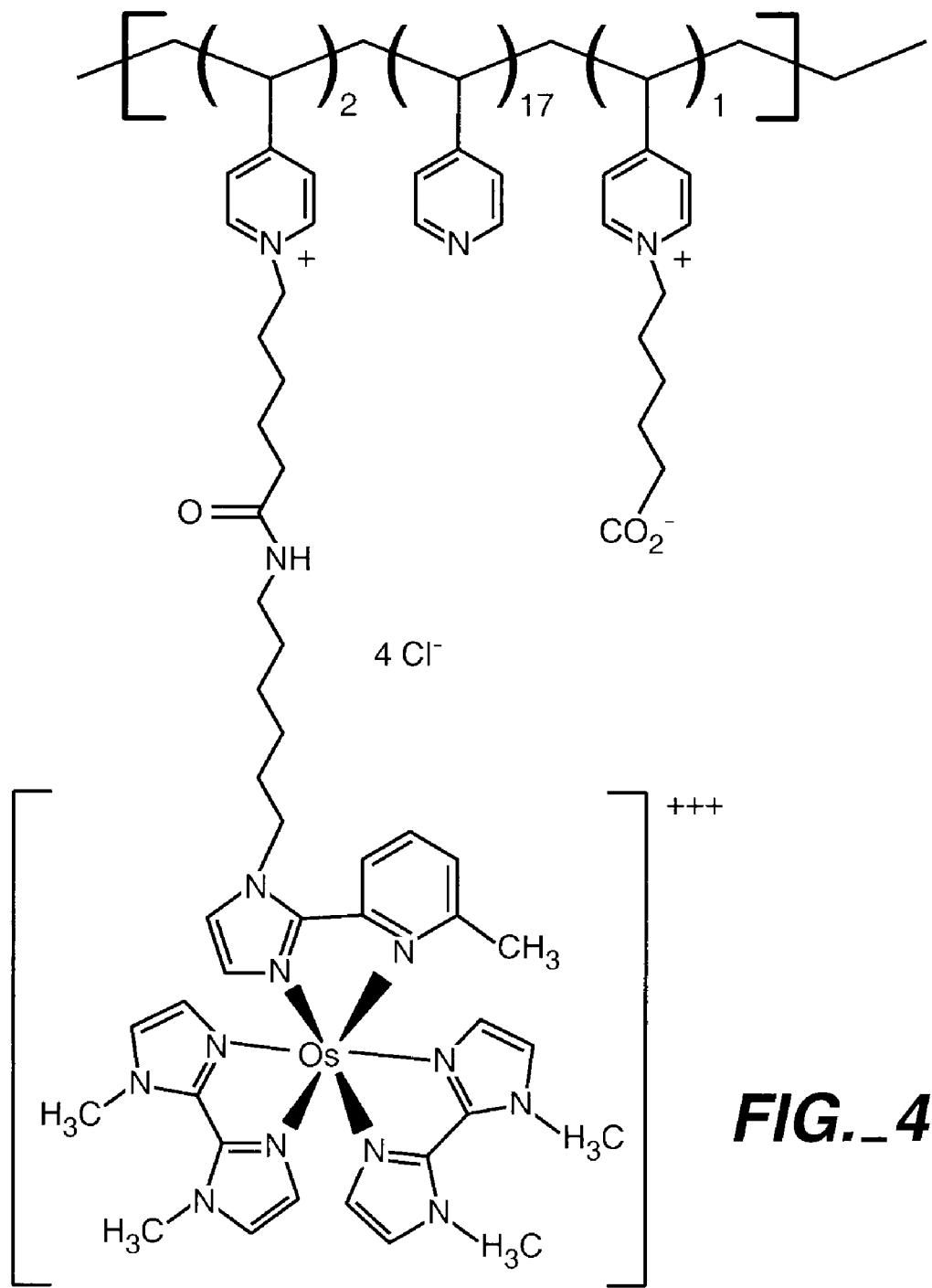
Structure of Redox Polymer 316
FIG._4B

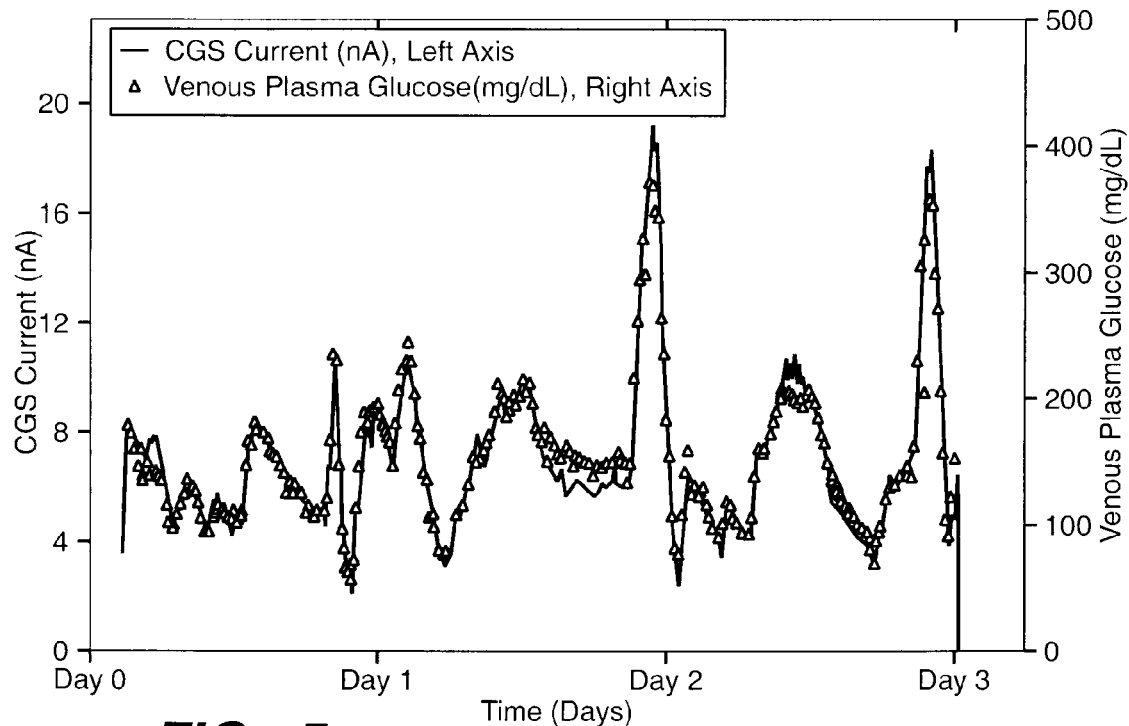
FIG._5
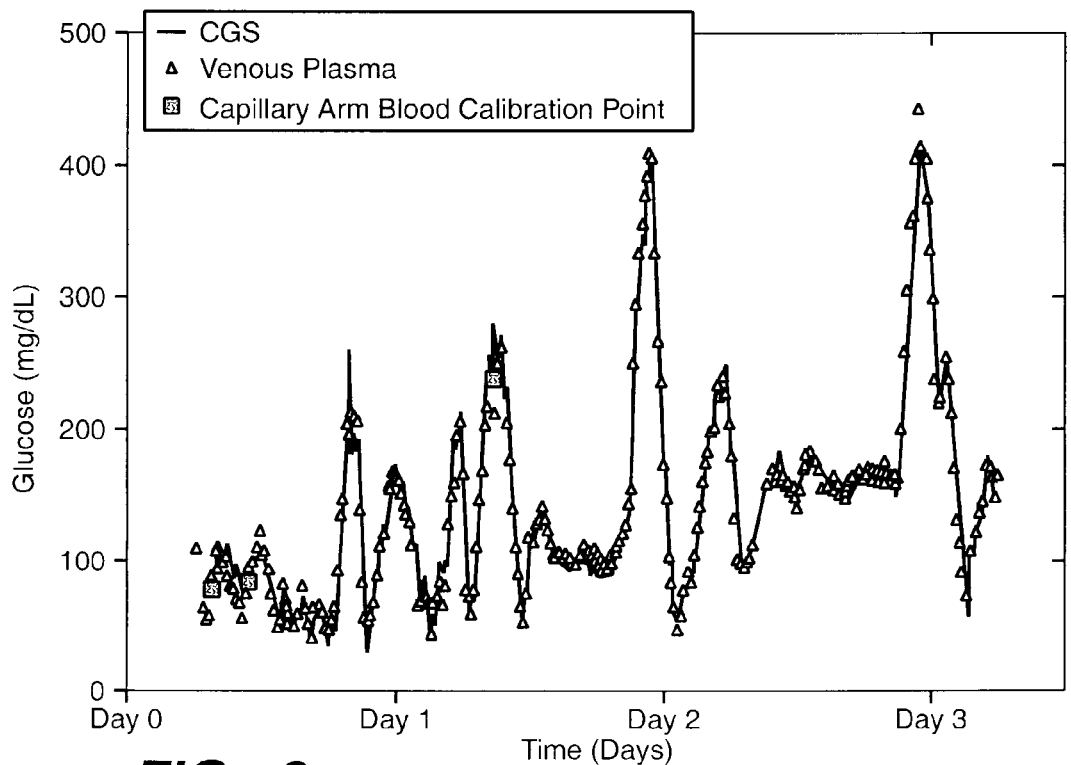
FIG._6

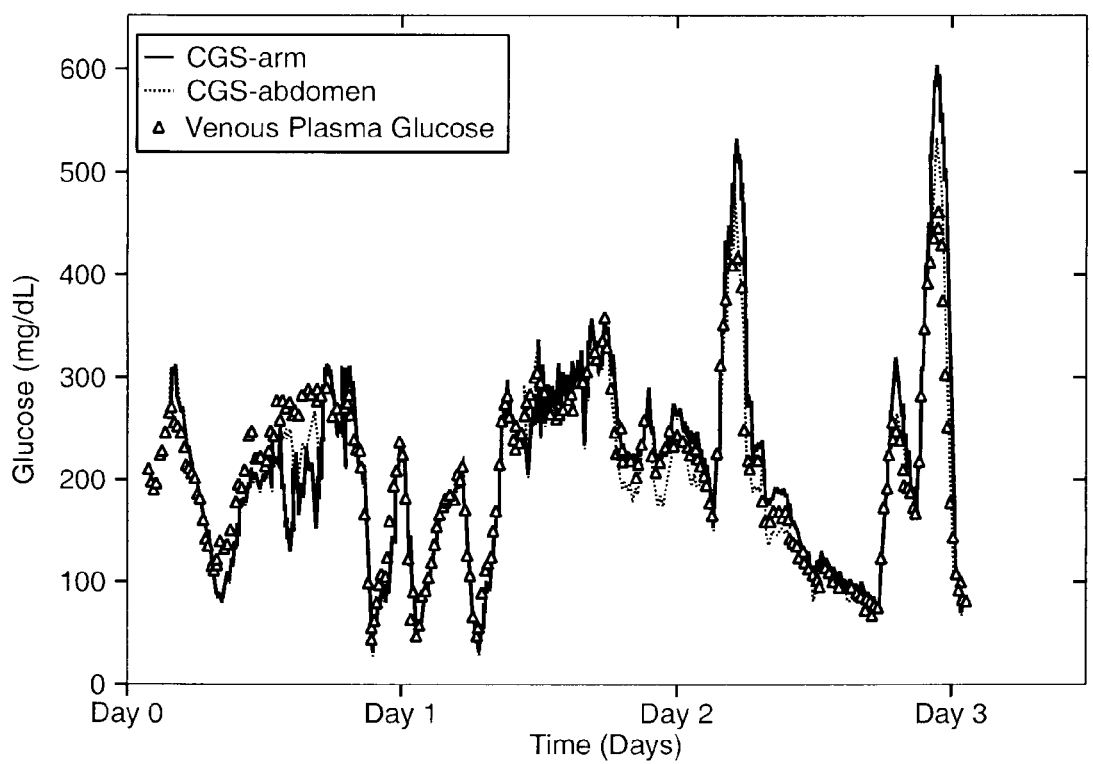
FIG._7
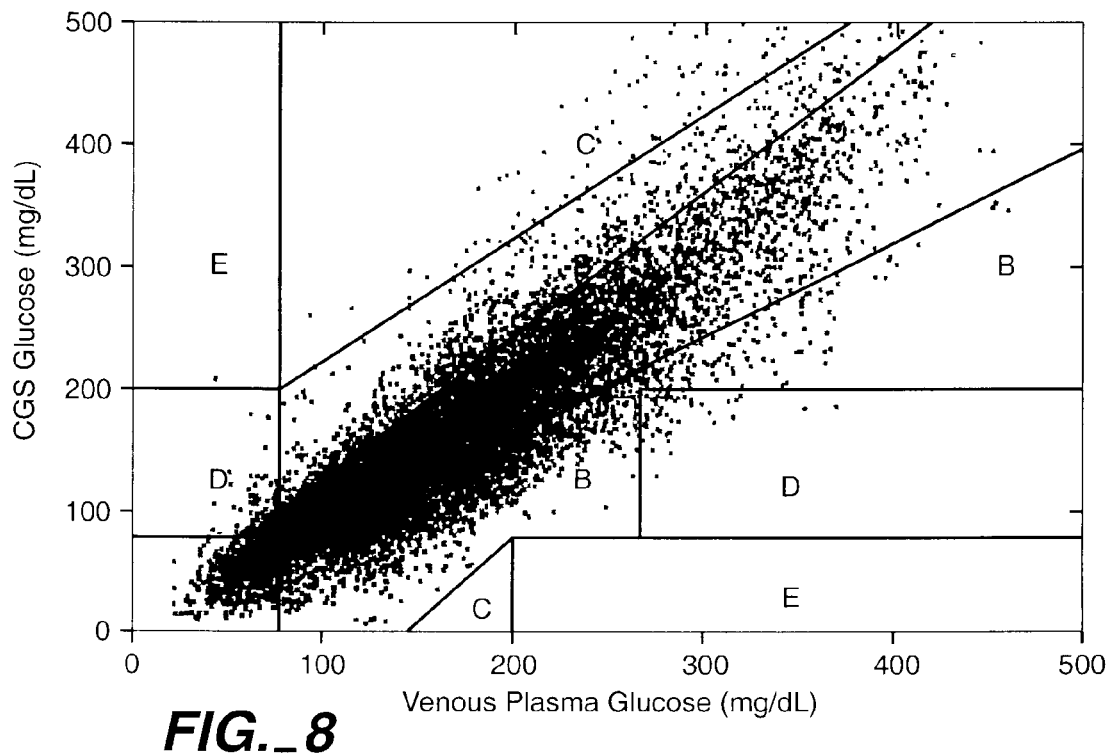
FIG._8

METHOD OF CALIBRATING AN ANALYTE-MEASUREMENT DEVICE, AND ASSOCIATED METHODS, DEVICES AND SYSTEMS

CROSS-REFERENCE TO RELATED APPLICATIONS

This application is a continuation application of U.S. patent application Ser. No. 11/929,149 filed Oct. 30, 2007 of Benjamin J. Feldman, et al., which is a continuation of U.S. patent application Ser. No. 10/975,207 filed Oct. 27, 2004, now U.S. Pat. No. 7,299,082, which is related to, and claims priority based on, U.S. Patent Application No. 60/516,599 of Feldman et al. (hereinafter, the "Feldman et al. Application") filed on Oct. 31, 2003, which is the subject of Feldman et al., *A Continuous Glucose Sensor Based on Wired Enzyme Technology-Results from a 3-Day Trial in Patients with Type I Diabetes*, Diabetes Technology & Therapeutics, Vol. 5, No. 5, pp. 769-779 (2003) (hereinafter, the "Feldman et al. Publication"). This application is also related to U.S. Pat. No. 6,881,551, which issued on Apr. 19, 2005; U.S. Pat. No. 6,551,494, which issued on Apr. 22, 2003; U.S. Pat. No. 6,514,718, which issued on Feb. 4, 2003; U.S. Pat. No. 6,175,752, which issued on Jan. 16, 2001; and U.S. Pat. No. 6,565,509, which issued on May 20, 2003. Each of the aforementioned applications, publications, and patents are incorporated herein in their entirety and for all purposes by this reference.

TECHNICAL FIELD

The invention relates to the calibration of an analyte-measurement device adapted to determine the concentration of an analyte in a fluid from a measurement site within a body, such as an animal body, a mammalian body, or a human body. The invention further relates to the use of a calibration standard that is based on a concentration of an analyte in blood from a calibration site that is not accessed through a surface of a fingertip, or is not accessed through a surface of the finger, or is not on or within a finger. The invention is particularly suited for calibrating partially or fully implantable glucose-monitoring devices, such as transcutaneous or subcutaneous glucose-monitoring devices. Devices, systems and kits making use of the aforementioned method are provided as well.

BACKGROUND

There are a number of instances when it is desirable or necessary to monitor the concentration of an analyte, such as glucose, lactate, or oxygen, for example, in a fluid of a body, such as a body of an animal. The animal may be a mammal, such as a human, by way of example. For example, it may be desirable to monitor the level of various analytes in bodily fluid, such as blood, that may have detrimental effects on a body.

In a particular example, it may be desirable to monitor high or low levels of glucose in blood that may be detrimental to a human. In a healthy human, the concentration of glucose in the blood is maintained between about 0.8 and about 1.2 mg/mL by a variety of hormones, such as insulin and glucagons, for example. If the blood glucose level is raised above its normal level, hyperglycemia develops and attendant symptoms may result. If the blood glucose concentration falls below its normal level, hypoglycemia develops and attendant symptoms, such as neurological and other symptoms, may result. Both hyperglycemia and hypoglycemia may result in death if untreated. Maintaining blood glucose at an appropriate concentration is thus a desirable or necessary part of treating a person who is physiologically unable to do so unaided, such as a person who is afflicted with diabetes mellitus.

Certain compounds may be administered to increase or decrease the concentration of blood glucose in a body. By way of example, insulin can be administered to a person in a variety of ways, such as through injection, for example, to decrease that person's blood glucose concentration. Further by way of example, glucose may be administered to a person in a variety of ways, such as directly, through injection or administration of an intravenous solution, for example, or indirectly, through ingestion of certain foods or drinks, for example, to increase that person's blood glucose level.

Regardless of the type of adjustment used, it is typically desirable or necessary to determine a person's blood glucose concentration before making an appropriate adjustment. Typically, blood glucose concentration is monitored by a person or sometimes by a physician using an in vitro test that requires a blood sample that is relatively large in volume, such as three microliters (µL) or more. The person may obtain the blood sample by withdrawing blood from a blood source in his or her body, such as a vein, using a needle and syringe, for example, or by lancing a portion of his or her skin, using a lancing device, for example, to make blood available external to the skin, to obtain the necessary sample volume for in vitro testing. (See U.S. Provisional Patent Application No. 60/424,414 of Saikley et al. filed on Nov. 6, 2002; and U.S. Patent Application Publication No. 2004/0138588 A1 of Saikley et al. filed on Nov. 4, 2003.) The person may then apply the fresh blood sample to a test strip, whereupon suitable detection methods, such as calorimetric, electrochemical, or photometric detection methods, for example, may be used to determine the person's actual blood glucose level. The foregoing procedure provides a blood glucose concentration for a particular or discrete point in time, and thus, must be repeated periodically, in order to monitor blood glucose over a longer period.

Since the tissue of the fingertip is highly perfused with blood vessels, a "finger stick" is generally performed to extract an adequate volume of blood for in vitro glucose testing. By way of example, a finger stick may involve lancing the fingertip and "milking" the adjacent tissue, such that an adequate volume of blood is available on the fingertip surface. Unfortunately, the fingertip is also densely supplied with pain receptors, which can lead to significant discomfort during the blood extraction process. Thus, conventional extraction procedures are generally inconvenient and often painful for the individual, particularly when frequent samples are required.

A less painful method for obtaining a blood sample for in vitro testing involves lancing an area of the body having a lower nerve ending density than the fingertip, such as the hand, the arm, or the thigh, for example. Such areas are typically less supplied, or not heavily supplied, with near-surface capillary vessels, and thus, blood. For example, a total blood flow of 33±10 mL/100 gm-min at 20° C. has been reported for fingertips, while a much lower total blood flow of 6 to 9 mL/100 gm-min has been reported for forearm, leg, and abdominal skin. (See: Johnson, *Peripheral Circulation*, John Wiley & Sons, p. 198 (1978).) As such, lancing the body in these regions typically produces sub-microliter samples of blood that are not sufficient for most in vitro blood glucose-monitoring systems.

Glucose-monitoring systems that allow for sample extraction from sites other than the finger and that can operate using small samples of blood, have been developed. For example, U.S. Pat. No. 6,120,676 to Heller et al. describes devices that permit generally accurate electrochemical analysis of an analyte, such as glucose, in a small sample volume of blood.

Typically, less than about one μL of sample is required for the proper operation of these devices, which enables glucose testing through "arm sticks" rather than finger sticks. Additionally, commercial products for measuring glucose levels in blood that is extracted from sites other than the finger have been introduced, such as the FreeStyle® blood glucose-monitoring system (Abbott Diabetes Care, formerly known as TheraSense, Inc., Alameda, Calif.) that is based on the above-referenced U.S. Pat. No. 6,120,676.

However, differences between the circulatory physiology of finger sites and "off-finger" sites have led to differences in the measurements of blood glucose levels associated with those different sites, as reported in McGarraugh et al., *Glucose Measurements Using Blood Extracted from the Forearm and the Finger*, TheraSense, Inc., Alameda, Calif. (2001), and McGarraugh et al., *Physiological Influences on Off-Finger Glucose Testing*, Diabetes Technology & Therapeutics, Vol. 3, No. 3, pp. 367-376 (2001). The former study indicates that stimulating blood flow at the skin surface of the arm may reduce these differences in certain circumstances when the off-finger site is the arm. In the latter study, the differences between blood glucose measurements using capillary blood from the finger and those using capillary blood from the arm were attributed to a time lag in the glucose response on the arm with respect to the glucose response on the finger that was observed when the glucose concentration was changing. This time lag varied from subject-to-subject in a range of five to twenty minutes. The study found that when glucose concentration is decreasing rapidly into a state of hypoglycemia, this time lag could delay the detection of hypoglycemia. Thus, it was determined that relative to the arm, the finger was a preferable test site for testing for hypoglycemia.

It follows that while it may be desirable to move away from the finger as a site for obtaining blood samples for discrete or periodic in vitro blood glucose determinations, in view of the pain involved, for example, it has not heretofore been deemed practical to do so to effectively monitor for low blood glucose levels that may be detrimental to an individual.

In addition to the discrete or periodic, in vitro, blood glucose-monitoring systems described above, at least partially implantable, or in vivo, blood glucose-monitoring systems, which are designed to provide continuous in vivo measurement of an individual's blood glucose concentration, have been described. (See, e.g., U.S. Pat. No. 6,248,067 to Causey et al.; U.S. Pat. No. 6,212,416 to Ward et al.; U.S. Pat. No. 6,175,752 to Say et al.; U.S. Pat. No. 6,119,028 to Schulman et al.; U.S. Pat. No. 6,091,979 to Pfeiffer et al.; U.S. Pat. No. 6,049,727 to Crothall et al.; and U.S. Pat. No. 5,791,344 to Schulman et al.; and International Publication No. WO 00/78992.) Although optical means or devices may be employed to monitor glucose concentration, a number of these in vivo systems are based on "enzyme electrode" technology, whereby an enzymatic reaction involving glucose oxidase is combined with an electrochemical sensor for the determination of an individual's blood glucose level. By way of example, the electrochemical sensor may be inserted into a blood source, such as a vein or other blood vessel, for example, such that the sensor is in continuous contact with blood and can effectively monitor blood glucose levels. Further by way of example, the electrochemical sensor may be placed in substantially continuous contact with bodily fluid other than blood, such as dermal or subcutaneous fluid, for example, for effective monitoring of glucose levels in such bodily fluid. Relative to discrete or periodic monitoring, continuous monitoring is generally more desirable in that it may provide a more comprehensive assessment of glucose levels and more useful information, such as predictive trend information, for example. Subcutaneous continuous glucose monitoring is also desirable for a number of reasons, one being that continuous glucose monitoring in subcutaneous bodily fluid is typically less invasive than continuous glucose monitoring in blood.

While continuous glucose monitoring is desirable, there are several drawbacks associated with the manufacture and calibration of continuous glucose-monitoring devices. By way of example, based on current manufacturing techniques, it may be impossible to account for sensor-to-sensor or subject-to-subject variability in performing accurate factory calibration. Further by way of example, individual-specific calibration may be desirable or required to account for subject-to-subject variability, such as subject-to-subject physiological variability. If an individual-specific calibration is called for, a sample of the individual's blood may be required in order to calibrate a glucose monitor for that individual's use.

Further development of calibration methods, as well as analyte-monitoring devices, systems, or kits employing same, is desirable.

SUMMARY OF THE INVENTION

The concentration of a specific analyte at one area of a body may vary from that at another area. Herein, a body refers to a body of an animal, such as a mammal, and includes a human. Such a variation may be associated with a variation in analyte metabolism, production, and/or transportation from one area of the body and another. When data obtained from one area of the body is used to calibrate an analyte-measurement or monitoring device for a particular individual, such a variation may result in improper calibration of the device for that individual. According to one aspect of the present invention, a method of calibrating such a device that accounts for such a variation, is provided.

For example, one aspect of the invention relates to a method for calibrating an analyte-measurement device that is adapted to evaluate the analyte concentration in a bodily fluid from a specific measurement site in a body. The method involves determining the concentration of the analyte in blood from a calibration site within the body that is not accessed through a surface of a fingertip, and, based on that determination, calibrating the analyte-measurement device. Preferably, the calibration site is not accessed through a surface of a finger. Most preferably, the calibration site is not on or within a finger. By way of example, but not limitation, the calibration site may be accessed through a surface of a palm, a hand, an arm, a thigh, a leg, a torso, or an abdomen, of the body, and may be located within a palm, a hand, an arm, a thigh, a leg, a torso, or an abdomen, of the body. An in vitro blood glucose-monitoring device, such as the above-mentioned FreeStyle® blood glucose-monitoring device, may be used for determining the concentration of the analyte in the blood from the calibration site, or an in vivo measurement device or sensor may be used. The analyte-measurement device undergoing calibration may be, and preferably is, an in vivo glucose-monitoring device, such as that described in U.S. Pat. No. 6,175,752 of Say et al. filed on Apr. 30, 1998, U.S. Pat. No. 6,329,161 of Heller et al. filed on Sep. 22, 2000, U.S. Pat. No. 6,560,471 of Heller et al. filed on Jan. 2, 2001, U.S. Pat. No. 6,579,690 of Bonnecaze et al. filed on Jul. 24, 2000, U.S. Pat. No. 6,654,625 of Say et al. filed on Jun. 16, 2000, and U.S. Pat. No. 6,514,718 of Heller et al. filed on Nov. 29, 2001, for example. It is contemplated that the analyte-measurement device may be an in vivo FreeStyle Navigator® glucose monitoring device (Abbott Diabetes Care Inc.), based on the foregoing U.S. Pat. Nos. 6,175,752, 6,329,161, 6,560,471, 6,579,690, 6,654,625, and 6,514,718, that is currently in clinical trials, though not now commercially available.

Another aspect of the invention relates to a method for monitoring the concentration of an analyte in a body. The method involves determining a concentration of the analyte in blood from a calibration site, such as that described above; inserting a sensor into the body at a specific measurement site; obtaining at least two signals indicative of the concentration of the analyte in the bodily fluid at that measurement site via the sensor; and adjusting those signals based on the concentration of the analyte in blood from the calibration site. An in vitro blood glucose-monitoring device, such as the above-mentioned FreeStyle® blood glucose-monitoring device, may be used for determining the concentration of the analyte in the blood from the calibration site, although in vivo measurement devices or sensors may also be used. The sensor is chosen as one that is sufficient for determining the concentration of the analyte in the bodily fluid at the measurement site, or providing a signal indicative of such analyte concentration, such as that associated with an in vivo glucose monitoring device, as described above. Preferably, the sensor is exposed to the bodily fluid in a thorough or substantially continuous manner. Preferably, obtaining the signals indicative of the concentration of the analyte in the bodily fluid at the measurement site occurs over a period of time, such as from about one day to about three days or more, for example.

According to yet another aspect of the invention, a surface of the body adjacent to the calibration site may be rubbed prior to the determination of analyte concentration in blood from the calibration site. Preferably, the rubbing is sufficient to enhance mobility of fluid at the calibration site. Typically, manually rubbing the surface of an arm, leg, or abdomen, for example, with a comfortable or moderate amount of pressure for a few seconds, up to a minute or more, will suffice to enhance mobility of fluid at a nearby calibration site within the arm, leg, or abdomen, respectively. Rubbing pressure and time can be varied appropriately, for example, less pressure can be applied for longer, and more pressure can be applied more briefly, and either or both can be varied as desirable or necessary for a particular calibration site. Any appropriate means or devices, manual or otherwise, may be used to rub the surface or to enhance mobility of the fluid at the calibration site.

A method according to the present invention is well suited for use in connection with a device that allows for the self-monitoring of glucose levels. Such a method may involve determining or measuring an analyte concentration in subcutaneous fluid, or in dermal fluid, or in interstitial fluid, for example. Any of the above-described methods may utilize any of a number of calibration sites in a body, such as those in the arms, the legs, the torso, the abdomen, or any combination thereof, merely by way of example. In humans, arms and legs are particularly convenient calibration sites. The measurement and calibration sites may be located in different parts of a body, or in the same region or regions of the body. The same or different types of devices may be used to measure analyte concentration in the bodily fluid and in the blood. Depending on the particular physiological conditions of the calibration site or sites, it may be desirable to rub a surface of the body adjacent the calibration site, such as arm skin that is above or near a calibration site within an arm, as previously described. (See: U.S. Pat. No. 6,591,125 of Buse et al. filed on Jun. 27, 2000.)

According to yet another aspect of the present invention, a system or kit for measuring the concentration of an analyte in a body is provided. The system comprises a measurement sensor for providing a signal indicative of a concentration of the analyte in the bodily fluid at the measurement site, a calibration sensor for determining a concentration of the analyte in blood from the calibration site, and a calibration device in operative communication with the measurement sensor and the calibration sensor for receiving data therefrom. The measurement sensor may be a disposable device, and may be independent, separate, separable or detachable relative to the calibration device, and may be wirelessly or physically associated with the calibration device when in use. Appropriate measurement sensors include the various in vivo measurement devices or sensors described above. The calibration sensor may be any sensor sufficient for determining the concentration of the analyte in blood at the calibration site. Appropriate calibration sensors include the various in vitro measurement devices or sensors described above, although in vivo measurement devices or sensors may also be used. The calibration device comprises a receiving element for receiving at least one signal obtained via the measurement sensor, a receiving element for receiving at least one concentration value obtained via the calibration sensor, and calibration element for calibrating the signal obtained via the measurement sensor based on the value obtained via the calibration sensor. The receiving element may comprise a storage element for storing any value received. The calibration element may comprise an algorithm for making the calibration or adjustment, which algorithm may be embodied in software.

Preferably, the measurement sensor is sufficient for electrochemically determining the concentration of the analyte in the bodily fluid. When an electrochemical measurement sensor is used, the sensor generally comprises a working electrode and a counter electrode. When the analyte of interest is glucose, the working electrode generally comprises a glucose-responsive enzyme and a redox mediator. The redox mediator may comprise an osmium (Os)- or a ruthenium (Ru)-containing complex, by way of example, preferably, the former. Preferably, the redox mediator is non-leachable relative to the working electrode, such that it does not leach from the working electrode into the body over the lifetime of the sensor. Most preferably, the redox mediator is immobilized on the working electrode.

Preferably, the calibration sensor is sufficient for electrochemically determining the concentration of the analyte in blood based on any suitable volume of blood. While this volume may be about 3 µL for some measurement sensors, as described above, it is preferably less than or equal to about 1 µL of blood, more preferably, less than or equal to about 0.5 µL of blood, and still more preferably, less than or equal to about 0.2 µL of blood, such as the smallest amount sufficient for a meaningful measurement. The calibration sensor may be an in vitro electrochemical sensor, as described above, or an in vivo electrochemical sensor, as also described above, designed for sensing in blood, typically and preferably the former.

These and various other aspects, features and embodiments of the present invention are further described herein.

BRIEF DESCRIPTION OF THE DRAWINGS

A detailed description of various aspects, features and embodiments of the present invention is provided herein with reference to the accompanying drawings, which are briefly described below. The drawings are illustrative and are not necessarily drawn to scale. The drawings illustrate various aspects or features of the present invention and may illustrate one or more embodiment(s) or example(s) of the present invention in whole or in part. A reference numeral, letter, and/or symbol that is used in one drawing to refer to a particular element or feature may be used in another drawing to refer to a like element or feature.

Each of FIG. 1A and FIG. 1B is a schematic illustration of a system or portions thereof for measuring a concentrate of an analyte in a bodily fluid that may be employed, according to various aspects of the present invention. These two figures may be collectively referred to as FIG. 1 herein.

FIG. 2A, FIG. 2B, and FIG. 2C, collectively and sequentially illustrate a calibration process or algorithm that may be employed, according to various aspects of the present invention. These three figures may be collectively referred to as FIG. 2 herein.

FIG. 3 is a schematic illustration of an analyte-measuring or monitoring device, a portion of which is enlarged for illustration purposes, that may be employed, according to various aspects of the present invention.

FIG. 4A is a schematic illustration of a sensing layer that is associated with a working electrode of an analyte-measuring or monitoring device, such as that illustrated in FIG. 3. FIG. 4B is an illustration of the structure of a redox polymer component of a sensing layer, such as that illustrated in FIG. 4A. FIGS. 4A and 4B may be collectively referred to as FIG. 4 herein.

FIG. 5 is a overlay plot of representative data (–) from an abdominally implanted analyte-measuring or monitoring device in raw, uncalibrated current (nA) on the left axis versus time (days) and venous plasma data (Δ) in glucose concentration (mg/dL) on the right axis versus time (days), according to an Experimental Study described herein.

FIG. 6 is a plot of representative data (–) from an arm-implanted analyte-measuring or monitoring device, as calibrated, venous plasma data (Δ), and arm-capillary blood data (□), in glucose concentration (mg/dL) versus time (days), according to an Experimental Study described herein.

FIG. 7 is a plot of representative data (–) from an arm-implanted analyte-measuring or monitoring device, as calibrated, representative data (–) from an abdomen-implanted analyte-measuring or monitoring device, as calibrated, and venous plasma data (Δ), in glucose concentration (mg/dL) versus time (days), according to an Experimental Study described herein.

FIG. 8 is a plot of glucose concentration data (mg/dL) from arm- or abdomen-implanted analyte-measuring or monitoring devices, as calibrated, versus that data from venous blood, in the form of a Clarke error grid, according to an Experimental Study described herein.

DETAILED DESCRIPTION OF THE INVENTION

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor designs or usages, unless implicitly or explicitly understood or stated otherwise, as such may vary.

The terms "amperometry" and "amperometrically" refer to the measurement of the strength of a current and include steady-state amperometry, chronoamperometry, and Cottrell-type measurements.

The term "bodily fluid" in the context of the invention encompasses all non-blood bodily fluid that can be found in the soft tissue of an individual's body, such as subcutaneous, dermal, or interstitial tissue, in which the analyte may be measured. By way of example, the term "bodily fluid" encompasses a fluid such as dermal, subcutaneous, or interstitial fluid.

The term "blood" in the context of the invention encompasses whole blood and its cell-free components, such as plasma and serum. The term "capillary blood" refers to blood that is associated with any blood-carrying capillary of the body.

The term "concentration" may refer to a signal that is indicative of a concentration of an analyte in a medium, such as a current signal, for example, to a more typical indication of a concentration of an analyte in a medium, such as mass of the analyte per unit volume of the medium, for example, or the like.

"Coulometry" refers to the determination of charge passed or projected to pass during complete or nearly complete electrolysis of a compound, either directly on the electrode or through one or more electron-transfer agents. The charge is determined by measurement of electrical charge passed during partial or nearly complete electrolysis of the compound or, more often, by multiple measurements during the electrolysis of a decaying current over an elapsed period. The decaying current results from the decline in the concentration of the electrolyzed species caused by the electrolysis.

A "counter electrode" refers to one or more electrodes paired with the working electrode, through which passes an electrochemical current equal in magnitude and opposite in sign to the current passed through the working electrode. The term "counter electrode" is meant to include counter electrodes that also function as reference electrodes (i.e., a counter/reference electrode) unless the description provides that a "counter electrode" excludes a reference or counter/reference electrode.

The term "electrolysis" refers the electrooxidation or electroreduction of a compound either directly at an electrode or via one or more electron-transfer agents, such as redox mediators and/or enzymes, for example.

An "immobilized" material refers to a material that is entrapped on a surface or chemically bound to a surface.

An "implantable" device refers to a fully implantable device that is implanted fully within a body and/or an at least partially implantable device that is at least partially implanted within a body. An example of an at least partially implantable sensing device is a transcutaneous sensing device, sometimes referred to as a subcutaneous sensing device, that is associated with a portion that lies outside of a body and a portion that penetrates the skin from the outside of the body and thereby enters the inside of the body.

The term "measure," as in "to measure the concentration," is used herein in its ordinary sense and refers to the act of obtaining an indicator, such as a signal, that may be associated with a value, such as concentration, for example, and to the act of ascertaining a value, such as a concentration, for example. The term "monitor," as in "to monitor the concentration," refers to the act of keeping track of more than one measurement over time, which may be carried out on a systematic, regular, substantially continuous, and/or on-going basis. The terms measure and monitor may be used generally herein, such as alternately, alternatively, or interchangeably, or more specifically, as just described.

The term "measurement" may refer to a signal that is indicative of a concentration of an analyte in a medium, such as a current signal, for example, to a more typical indication of a concentration of an analyte in a medium, such as mass of the analyte per unit volume of the medium, for example, or the like. The term "value" may sometimes be used herein as a term that encompasses the term "measurement."

The term "patient" refers to a living animal, and thus encompasses a living mammal and a living human, for example. The term "subject" may sometimes be used herein as a term that encompasses the term "patient."

The term "redox mediator" refers to an electron-transfer agent that transfers electrons between a compound and a working electrode, either directly or indirectly.

The term "reference electrode" encompasses a reference electrode that also functions as a counter electrode (i.e., a counter/reference electrode), unless the description provides that a "reference electrode" excludes a counter/reference electrode.

The term "working electrode" refers to an electrode at which a candidate compound is electrooxidized or electroreduced with or without the agency of a redox mediator.

The invention generally relates to the calibration of a device adapted to measure or monitor a concentration of an analyte in a body. The invention exploits a correspondence that exists between a concentration of an analyte found in a bodily fluid of an individual and a concentration of the same analyte found in blood of that individual. For example, according to the present invention, a concentration of an analyte in blood from a particular calibration site within the body of an individual is used to calibrate a device that is adapted to measure or monitor a concentration of the analyte at a measurement site in the body of that individual.

As previously described, it is often undesirable or painful to obtain blood from a fingertip or finger. The calibration method of the present invention does not demand this. That is, according to the present invention, a calibration site may be selected as one that is not accessed from a surface of a fingertip, one that is not accessed from a surface of a finger, or one that is not on or within a finger, preferably the latter. Merely by way of convenience, but not limitation, such a calibration site may be referred to as an "off-finger" calibration site. By way of example, but not limitation, the calibration site may be accessed through a surface of a palm, a hand, an arm, a thigh, a leg, or an abdomen, of the body, and may be located within a palm, a hand, an arm, a thigh, a leg, or an abdomen, of the body, or any other bodily site wherein the blood or capillary blood at the site generally tracks bodily fluid in terms of glucose concentration. The off-finger calibration site is typically located up to about 2 mm beneath the exterior surface of the epidermis, or up to the maximum depth appropriate for a "stick" by a lancet or other appropriate means or device.

As previously described, there are a number of different systems that can be used in the measuring or monitoring of glucose levels in a body, including those that comprise a glucose sensor that is adapted for insertion into a subcutaneous site within the body for the continuous monitoring of glucose levels in bodily fluid of the subcutaneous site. For example, U.S. Pat. No. 6,175,752 to Say et al. employs such a sensor that comprises at least one working electrode that is associated with a redox enzyme, wherein the redox enzyme is sufficient to catalyze a reaction that is associated with the detection of glucose. This sensor further comprises a counter electrode and a reference electrode, or a combined counter/reference electrode, and may further comprise a temperature probe. Such a sensor is further described in the Experimental Study below.

A suitable sensor may work as now described. The sensor is placed, transcutaneously, for example, into a subcutaneous site such that subcutaneous fluid of the site comes into contact with the sensor. The sensor operates to electrolyze an analyte of interest in the subcutaneous fluid such that a current is generated between the working electrode and the counter electrode. A value for the current associated with the working electrode is determined periodically. If multiple working electrodes are used, current values from each of the working electrodes may be determined periodically. A microprocessor may be used to collect these periodically determined current values or to further process these values.

The periodically determined current values may be processed in various ways. By way of example, current values may be checked to determine whether they are within a predetermined range. If the current values are within the predetermined range, one of the current values is converted to an analyte concentration by way of a calibration. Further by way of example, in the case of multiple working electrodes, current values from each of the working electrodes may be compared to determine whether they differ by a predetermined threshold amount. If the current values are within the predetermined range and do not differ by more than the predetermined threshold amount, one of the current values is converted to an analyte concentration by way of a calibration. Sensor-specific calibration may be performed during the manufacture of the sensor, as described elsewhere herein. Alternative or additional individual-specific calibration may be performed on an individual basis, as also described herein. Further calibration may be needed when the current values from a working electrode or from each of multiple working electrodes are not within the predetermined range, or when the current values from each of multiple working electrodes differ by more than the predetermined threshold amount. If the current values do not meet one or more of the established criteria, none of the current values may be acceptable for conversion into an analyte concentration. An indication, such as a code, may be displayed or otherwise transmitted, such as via audio, visual, vibrational, sensory, or other suitable notification means or device, to indicate this fact. If analyte concentration is successfully determined, it may be displayed, stored, and/or otherwise processed to provide useful information. By way of example, analyte concentrations may be used as a basis for determining a rate of change in analyte concentration, which should not change at a rate greater than a predetermined threshold amount. If the rate of change of analyte concentration exceeds the predefined threshold, an indication may be displayed or otherwise transmitted to indicate this fact.

The sensor may have undergone calibration during the manufacturing process. However, as previously described, such calibration may be insufficient in terms of accounting for sensor-to-sensor or subject-to-subject variability. Thus, individual-specific calibration may be desirable or required to account for subject-to-subject variability, such as subject-to-subject physiological variability. In such a calibration, a sample of blood may be extracted from a calibration site within the individual and measured to obtain a glucose concentration for use as a calibration point. The measurement may be carried out using any of various known means, devices and methods, such as via the FreeStyle® blood glucose-monitoring system. The resulting glucose concentration can be entered into an analyte-monitoring device as a calibration code, as desirable or needed, for example, immediately after sensor implantation or following notification of an invalid result. The sensor may be calibrated manually, periodically, or as desirable or necessary, during use.

As described above, blood samples are often obtained from sites within highly perfused areas of the body, such as sites within the fingertips. Blood-sampling from these sites is quite painful. Alternative sites, however, have not previously been thought to be sufficiently practical or useful as sources for calibration samples. By way of example, in a previous study, it was reported that capillary blood obtained simultaneously from different body sites have different glucose concentrations, and that the blood glucose levels obtained from the arm and the finger were not perfectly correlated. (See: McGarraugh et al., *Glucose Measurements Using Blood Extracted from the Forearm and the Finger*, TheraSense, Inc., Alameda, Calif. (2001); and McGarraugh et al., *Physiological Influences on Off-Finger Glucose Testing*, Diabetes Technology & Therapeutics, Vol. 3, No. 3, pp. 367-376 (2001).) Thus, it has previously been thought that alternative sites are not suitable for blood-sampling for calibration purposes.

According to the present invention, blood-sampling at alternative sites is used for calibration purposes. As demonstrated in the Experimental Study described herein, the use of alternative sites for calibration purposes is advantageous for a number of reasons beyond pain reduction, such as allowing for the concentration of calibration points early on in the period of use, allowing for the refinement of calibration as multiple calibration points are obtained, allowing for the use of real-time data, and providing clinically accurate or acceptable results.

According to an embodiment of the present invention, a method for calibrating a device sufficient for determining a concentration of an analyte of interest at a measurement site within a body, comprises providing the device at the measurement site within the body, determining a concentration of the analyte in blood from an off-finger calibration site within the body, and calibrating the device using the resulting analyte concentration. According to this method, the resulting analyte concentration may serve as a baseline concentration of analyte in the blood for calibration purposes. There is no particular limitation on the location of the measurement site. By way of example, any measurement site of practical utility may be used. Preferably, the measurement site is also an off-finger measurement site, such as an arm, a leg, a torso, or an abdomen, for example. The measurement site is typically located up to about 8 mm beneath the exterior surface of the epidermis, preferably located from about 2 mm to about 6 mm beneath the exterior surface, and more preferably located from about 3 mm to about 5 mm beneath the exterior surface.

According to another embodiment of the present invention, a method for determining a concentration of an analyte, such as glucose, in a bodily fluid at a measurement site within a body, comprises inserting a device, such as those described herein, at the measurement site within the body, determining the concentration of an analyte of interest, such as glucose, in blood from an off-finger calibration site within a body, and calibrating the device using the resulting analyte concentration. In this method, the sensor is used to determine at least two values for the concentration of the analyte in the bodily fluid at the measuring site. Further, calibrating the device comprises adjusting the at least two values based on the concentration of the analyte in blood from the calibration site. According to this method, the concentration of the analyte in blood from the calibration site may be determine at least once, or at least twice, during the determination of the at least two values for the concentration of the analyte in the bodily fluid at the measurement site. Here again, there is no particular limitation on the location of the measurement site, although preferably it is an off-finger site, such as an arm, a leg, a torso, or an abdomen, for example.

As demonstrated herein, the methods of the present invention are particularly useful in connection with a device that is used to measure or monitor a glucose analyte, such as any such device described herein. These methods may also be used in connection with a device that is used to measure or monitor another analyte, such as oxygen, carbon dioxide, proteins, drugs, or another moiety of interest, for example, or any combination thereof, found in bodily fluid, such as subcutaneous fluid, dermal fluid (sweat, tears, and the like), interstitial fluid, or other bodily fluid of interest, for example, or any combination thereof. Preferably, the device is in good contact, such as thorough and substantially continuous contact, with the bodily fluid.

According to yet another embodiment of the present invention, a system or kit for measuring a concentration of an analyte in a bodily fluid at a measurement site within the body is provided. An example of such a system 100 is schematically illustrated in FIG. 1A and FIG. 1B. The system 100 comprises a measurement sensor 102, a calibration sensor 104, and a calibration device 106. The measurement sensor 102 is any suitable sensor that is sufficient for determining the concentration of the analyte in the bodily fluid at a measurement site within the body, such as any described herein. The calibration sensor 104 is any suitable sensor that is sufficient for determining a calibration concentration of the analyte in blood at an off-finger calibration site within the body. The location of the measurement sensor within the body is unrestricted, although some locations may be more desirable or practical, as described above. Preferably, the measurement site is an off-finger site.

The two sensors 102 and 104 may be completely independent, such as an independent in vivo, continuous, glucose monitoring sensor and an independent in vitro, discrete, glucose-testing strip, that are physically separate, merely by way of example. The sensors 102 and 104 may be provided in a system or kit 100 that comprises elements sufficient for calibration and use of the measurement sensor according to the present invention, such as the elements described below.

The measurement sensor 102 and the calibration device 106 may be physically associated with one another, whether temporarily, detachably, or permanently. The measurement sensor 102 and the calibration device 106 may be wirelessly associated, whether directly (not shown) or indirectly, as shown via transmission element 108 in FIG. 1A. The measurement sensor 102 may include a transmission element or device 108 as a component (not shown), or may be operatively coupled to a transmission element or device 108, as shown in FIG. 1A and FIG. 1B. The coupling may be wireless or in the form of a direct physical connection, as shown in FIG. 1A, merely by way of example. The transmission element or device 108 is of a construction sufficient for receiving a raw analyte signal (represented by an encircled ~ symbol) from the measurement sensor 102 and transmitting a raw analyte signal, such as a current, for example, to the calibration element or device 106. The transmission device 108 and the calibration device 106 are operatively coupled for communication therebetween. The coupling may be in the form of a wireless connection, as shown in FIG. 1A, any other suitable communicative connection, or any combination thereof.

The calibration sensor 104 may include the calibration device 106 as a component (not shown), or may be operatively coupled to the calibration device 106, as shown in FIG. 1A and FIG. 1B. The coupling may be wireless (not shown) or in the form of a direct physical connection, as shown in FIG. 1A, merely by way of example. Preferably, the calibration device 106 is designed to receive calibration data from the calibration sensor 104 automatically, rather than manually via the user, so as to reduce the chances of data entry error, for example.

As shown in FIG. 1B, the calibration device 106 comprises an element 110 for receiving at least one signal or concentration value obtained via the measurement sensor 102 and an element 112 for receiving at least one concentration value obtained via the calibration sensor 104, and a calibration element 114 for evaluating data, such as a signal or value from the measurement sensor 112, and/or a value from the calibration sensor 104. The receiving elements 110 and 112 may comprise any suitable electronic circuitry, componentry, storage media, such as temporary storage media or rewriteable storage media, a signal- or data-processing element, a software element, or any combination thereof, merely by way of example, and may be physically (wired, for example) or wirelessly associated with sensors 102 and 104, respectively. The calibration element 114 may comprise any suitable electronic circuitry, componentry, storage media, an algorithmic element, a data-processing element, a software element, or any combination thereof, for making the adjustment or calibration. The calibration element 114 may comprise any suitable means or device for storing any suitable algorithm or software, such as any suitable storage media, for example, non-rewriteable electronic storage media and/or read-only electronic storage media. As output 110, the calibration element 114 may provide an indication of operating sensitivity 116, as shown in FIG. 1B, by way of example, for use in another part of the system, such as a microprocessor ("µP") 118, for calibrating an analyte signal or value from the measurement sensor based on the value from the calibration sensor, or calculating analyte concentration. The calibration, or calculation of analyte concentration, may be found by dividing the raw analyte signal by the operating sensitivity, when the sensitivity is expressed in appropriate units of current/concentration, such as nA/(mg/dL), for example. The system 100 may further comprise any suitable communication means or device (not shown), operatively connected to the microprocessor 118, for communicating the analyte sensitivity to the user, to another system, and/or the like.

Preferably, the measurement sensor 102 is designed, constructed, or configured for ease in self-monitoring analyte concentration in bodily fluid. Merely by way of example, the measurement sensor 102 may be any suitable sensor described in U.S. Pat. No. 6,175,752 to Say et al. The measurement sensor 102 may be one suited for an in vitro measurement of analyte concentration in solution, or one suited for in vivo measurement of analyte concentration of a bodily fluid. Merely by way of example, the measurement sensor 102 may be one suited for partial or full implantation within a body, such as an in vivo sensor suited for continuous monitoring of an analyte concentration in a bodily fluid with the body. The measurement sensor 102 may comprise an analyte-diffusion-limiting membrane, as further described in relation to the Experimental Study herein, although such a membrane is not required. (See: U.S. Pat. No. 6,932,894 of Mao et al. filed on May 14, 2002 (may include a membrane); and U.S. Pat. No. 7,052,591 of Gao et al. filed on Sep. 19, 2000 (may not include a membrane).)

According to a preferred embodiment of the present invention, the measurement sensor 102 is one suited for electrochemical measurement of analyte concentration, and preferably, glucose concentration, in a bodily fluid. In this embodiment, the measurement sensor 102 comprises at least a working electrode and a counter electrode. It may further comprise a reference electrode, although this is optional. The working electrode typically comprises a glucose-responsive enzyme and a redox mediator, as further described below in the Experimental Study, both of which are agents or tools in the transduction of the analyte, and preferably, glucose. Preferably, the redox mediator is non-leachable relative to the working electrode. Merely by way of example, the redox mediator may be, and preferably is, immobilized on the working electrode.

According to a most preferred embodiment of the present invention, the measurement sensor 102 is one suited for in vivo, continuous, electrochemical measurement or monitoring of analyte concentration, and preferably, glucose concentration, in a bodily fluid. In this embodiment, the measurement sensor 102 is sufficiently biocompatible for its partial or full implantation within the body. By way of explanation, when an unnatural device is intended for use, particularly long-term use, within the body of an individual, protective mechanisms of the body attempt to shield the body from the device. (See co-pending U.S. application Ser. No. 10/819,498 of Feldman et al. filed on Apr. 6, 2004, published as U.S. Publication No. 2005/0173245.) That is, such an unnatural device or portion thereof is more or less perceived by the body as an unwanted, foreign object. Protective mechanisms of the body may encompass encapsulation of the device or a portion thereof, growth of tissue that isolate the device or a portion thereof, formation of an analyte-impermeable barrier on and around the device or a portion thereof, and the like, merely by way of example. Encapsulation and barrier formation around all or part of the implantable sensor may compromise, significantly reduce, or substantially or completely eliminate, the functionality of the device. Preferably, the measurement sensor 102 is sufficiently biocompatible to reduce, minimize, forestall, or avoid any such protective mechanism or its effects on the sensor functionality, or is associated with or adapted to incorporate a material suitable for promoting biocompatibility, such as a superoxide-dismutase/catalase catalyst. (See co-pending U.S. application Ser. No. 10/819,498 of Feldman et al. filed on Apr. 6, 2004.) Preferably, the measurement sensor 102 is sufficiently biocompatible over the desired, intended, or useful life of the sensor.

It is also preferable that the measurement sensor 102 be relatively inexpensive to manufacture and relatively small in size. It is particularly preferable that the measurement sensor 102 be suitable for being treated as a disposable device, such that the measurement sensor may be disposed of and replaced by a new measurement sensor, for example. As such, the measurement sensor 102 is preferably physically separate from, or separable from, the calibration device 106 or calibration sensor 104. A measurement sensor suitable for operating over a period of about 1 to 3 days, is desirable. A measurement sensor suitable of operating over a longer period is contemplated, provided it provides no significant ill effect in the body.

The calibration device 106 may comprise suitable electronic and other components and circuitry such as those described in U.S. Pat. No. 6,175,752 to Say et al. By way of example, the calibration device 106 may comprise a potentiostat/coulometer suitable for use in connection with an electrochemical measurement sensor. The calibration device 106 may be a device that is suitable for repeated or on-going use, even if the measurement sensor 102 is disposable. As such, the measurement sensor 102 and the calibration device 106 may be physically separate or capable of physical separation or detachment.

According to embodiments of the present invention, the calibration site may be any off-finger site within a body that is a suitable source of blood or capillary blood. Convenient calibration sites may be those that are close to an exterior surface of the body. Preferred calibration sites are those that have a sufficient supply of blood or capillary blood for drawing a suitable sample and have a low density of pain receptors. Suitable calibration sites are located in an arm, a forearm, a leg, or a thigh, for example. Any suitable way or means of, or device for, measuring analyte concentration in blood or capillary blood at such a calibration site, such as any of those described herein, is contemplated as being of use according to the present invention. However, as obtaining a sufficient volume of blood for measurement may be more difficult at an off-finger calibration site than at a fingertip or finger calibration site, a suitable way or means of, or device for, measuring analyte concentration in a small volume of blood or capillary blood from an off-finger calibration site is preferred. A suitable way or means or device may be any of those associated with a small volume, in vitro, analyte sensor, such as any of those described in U.S. Pat. No. 6,120,676 to Heller et al.; or any of those suitable for measuring analyte concentration in preferably less than or equal to about 1 µL of blood or capillary blood, more preferably, less than or equal to about 0.5 µL of blood, and most preferably, less than or equal to about 0.2 µL of blood is used for calibration, such as any amount sufficient for obtaining a meaningful or useful measurement. In a preferred embodiment, such a way or means or device is electrochemical, such as amperometric or coulemetric, for example.

According to embodiments of the present invention, the measurement site may be any site within a body that is a suitable source of bodily fluid. A suitable measurement sites is any such site that is suitable for operation of the analyte-measurement or monitoring device. By way of example, suitable measurement sites include those in an abdomen, a leg, a thigh, an arm, an upper arm, or a shoulder, as described in U.S. Pat. No. 6,175,752 to Say et al. Preferably, the measurement site is in the upper arm or in the abdomen. The measurement site and the calibration sites may be located in substantially the same region or part of the body or in different regions or parts of a body.

The analyte-monitoring device may be calibrated a particular point or at various points in the analyte-monitoring process. The device is typically calibrated before it is used to monitor analyte concentration in a body. As such, analyte concentration in blood or capillary blood from the calibration site is typically measured within about five minutes to about one hour of sensor use or insertion within a body. In some cases, it may be desirable or necessary to calibrate the device during a period of analyte monitoring. As such, analyte concentration in blood or capillary blood may be measured once or more during such a period. Any suitable way or means of, or device for, measuring analyte concentration in a bodily fluid at a measurement site may be used. A suitable way or means or device may be electrochemical, as described above in connection with calibration measurements, albeit adapted as desirable or necessary for the measurement of analyte concentration in the bodily fluid rather than in blood.

Calibration may be described as a process by which a raw signal from an analyte-measuring or monitoring sensor is converted into an analyte concentration. By way of example, when an optical analyte sensor is used, the raw signal may be representative of absorbance, and when an electrochemical analyte sensor is used, the raw signal may be representative of charge or current. Calibration may generally be described in terms of three parts or phases, as described below.

In one phase, or a first phase, a calibration measurement may be made via a calibration sensor and a raw signal may be gathered via an analyte sensor more or less simultaneously. By more or less simultaneously, or substantially simultaneously, is meant within a period of up to about 10 minutes; preferably, up to about 5 minutes; more preferably, up to about 2 minutes; and most preferably, up to about 1 minute, in this context. In general, the calibration measurement is deemed or trusted as accurate because the performance of the calibration sensor has been verified through its own calibration process. Ideally, the calibration measurement and the raw signal are obtained from identical samples. Practically, this is often not possible. In the latter case, the relationship between the calibration sample and the test sample must be sufficiently strong to provide accurate or reliable results. By way of example, when blood glucose test strips are calibrated, the test sample may be capillary blood, while the calibration may be capillary plasma. Further by way of example, when subcutaneous glucose sensors are calibrated, the test sample may be subcutaneous fluid, while the calibration sample may be capillary blood.

In another phase, or a second phase, the quality of the raw analyte signal and the calibration measurement data are evaluated to determine whether to accept or decline a particular data pair for use in calibration. By way of example, dual calibration measurements may be made, and acceptance may be based upon adequate agreement of the dual measurements. Further by way of example, acceptance of the raw analyte signal may be predicated on some feature of that signal, such as magnitude or variability, for example. In the simplest manifestation of this phase of the calibration process, raw analyte signal and calibration measurement data pairs may be accepted without further discrimination.

In yet another phase, or a third phase, the raw analyte signal is converted into an analyte concentration. By way of example, when an electrochemical glucose sensor is used, a raw current signal (in nanoAmperes (nA), for example) may be converted into a glucose concentration (in units of mg/dL, for example). A simple way of performing this conversion is by simply relating or equating the raw analyte signal with the calibration measurement, and obtaining a conversion factor (calibration measurement/raw analyte signal), which is often called the sensitivity. Another simple way of performing this conversion is by assuming a sensitivity, such as a sensitivity based on a code associated with the measurement sensor, as described above. The sensitivity may be used to convert subsequent raw analyte signals to analyte concentration values via simple division ((raw analyte signal)/(sensitivity)=analyte concentration). For example, a raw analyte signal of 10 nA could be associated with a calibration analyte concentration of 100 mg/dL, and thus, a subsequent raw analyte signal of 20 nA could be converted to an analyte concentration of 200 mg/dL, as may be appropriate for a given analyte, such as glucose, for example. This is often called one-point calibration.

There are many variations of the conversion phase of the calibration process, as will be appreciated. Merely by way of example, the sensitivity can be derived from a simple average of multiple analyte signal/calibration measurement data pairs. Further by way of example, the sensitivity can be derived from a weighted average of multiple analyte signal/calibration measurement data pairs. Yet further by way of example, the sensitivity may be modified based on an empirically derived weighting factor, or the sensitivity may be modified based on the value of another measurement, such as temperature. It will be appreciated that any combination of such approaches, and/or other suitable approaches, is contemplated herein.

Ideally, the calibration measurement of the first phase described above is performed at the time of the analyte sensor is manufactured. Typically, representative sensors from a large batch or "lot" of analyte sensors are tested at the site of manufacture, and a calibration code is assigned to the sensor lot. The calibration code may then be used in association with the analyte-measuring device to convert the raw analyte signal into an analyte concentration. By way of example, a manufacturer or user of the device may enter the code into the device, or a data processor of the device, for such data conversion. Blood glucose test strips are typically calibrated in this manner, at the site of manufacture.

For other types of sensors, including subcutaneous glucose sensors, calibration at the site of manufacture is typically not feasible. This infeasibility may be based on any of a number of factors. Merely by way of example, variations in the within-lot performance of the analyte sensors may be too large, and/or variations in person-to-person response to a given sensor lot may be too large. When calibration at the site is not feasible, the calibration measurement must be performed upon fluid, often capillary blood, drawn from or within the wearer of the subcutaneous sensor. Such a calibration process is often called in vivo calibration.

An example of a calibration process 200 is now described in relation to a flow-chart illustration shown in FIGS. 2A, 2B, and 2C (collectively, FIG. 2). The process 200 comprises the selection 202 of at least one possible calibration point and the starting 204 of the process with the first possible calibration point. Merely by way of example, one may select three different calibration points and choose the first calibration point in time for further processing, such as a calibration point that is taken within or up to about one hour from the implantation of a measurement sensor, for example.

The first calibration point is then evaluated in at least one of several possible processes. For example, the calibration point may be evaluated as to whether or not (1) a predetermined time has elapsed since implantation or since a prior calibration 206, such as a predetermined time of about one hour after implantation, or a predetermined time of about 2 hours after a prior calibration, for example; (2) an analyte concentration ("[G]" in FIG. 2)) associated with the calibration point, such as an analyte concentration from a calibration sensor (for example, from an in vitro measurement of blood from the calibration site) falls within a predetermined range 208, such as a predetermined glucose concentration range of from about 60 to about 350 mg/dL, for example; (3) a rate of change in analyte concentration from an analyte sensor (for example, from an in vivo measurement of bodily fluid at the measurement site) since a prior calibration, over a predetermined period, such as about 10 minutes, or about 30 minutes, for example, falls within a predetermined range 210, in any direction (i.e., positive or negative, up or down), such as a predetermined range for a rate of change in glucose concentration change of up to about 2 (mg/dL)/minute, for example; (4) a temperature measurement, such as a measurement of skin temperature, for example, is within a predetermined range 212, such as a predetermined range of from about 28° C. to about 37° C., for example; and/or (5) the sensitivity falls within predetermined limits 214, such as within a preset range associated with an analyte sensor production lot 216 (for example, a preset range of percentage determined by a code assigned to a glucose sensor production lot). The evaluations associated with the rate of change in analyte concentration and the sensitivity are deemed of particular relevance for applications in which glucose is the analyte of interest.

If any of the evaluation standards is not met, the calibration point is deemed unacceptable 218, the next possible calibration point, if any, is selected 220, and that calibration point is then evaluated, as described above. If there is no next possible calibration point, the calibration process has failed to provide an acceptable calibration point and ends (not shown). If all of the evaluation standards are met, the calibration point is deemed acceptable 222. If there are more calibration points to evaluate 224, the next possible calibration point is selected 220, and that calibration point is then evaluated, as described above. If there are no more calibration points to evaluate 224, the sensitivity factor or factors are calculated 226, in any of a number of ways. Merely by way of example, an unweighted sensitivity factor (SN), such as the current from an analyte sensor (for example, from an in vivo measurement of bodily fluid at the measurement site) divided by the analyte concentration from a calibration sensor (for example, from an in vitro measurement of blood from the calibration site), may be determined for each calibration point 228; an adjusted weighting factor (AXM,N), based on a raw weighing factor (XM,N) and a sensitivity weighing factor (SWF), for example, may be determined for each calibration point 230; and/or a weighted sensitivity (WSN), based on a sensitivity fudge factor (FN), for example, may be determined for each calibration point 232, wherein N is the number associated with the calibration point (i.e., N=1 for the first calibration point 1, N=2 for next calibration point 2, N=3 for the next calibration point 3, etc.) and M is a number from 1 to N, inclusive (i.e., when N=1, M=1; when N=2, M=1 and M=2, such that there are two raw weighing factors and two adjusted weighting factors; when N=3, M=1, M=2, and M=3, such that there are three raw weighing factors and three adjusted weighting factors, etc.).

Based on at least one sensitivity factor, the analyte concentration value or values, such as a glucose concentration value, for example, is determined 234. By way of example, a raw glucose value (G-raw) may be calculated 236, where the raw glucose value equals the raw analyte signal (I), which may be a current from an analyte sensor, as described above, divided by an applicable weighted sensitivity (WS) value. Further by way of example, a temperature-compensated glucose value (G-temp) may be calculated 238, where this value equals the raw glucose value (G-raw), as just described, multiplied by a temperature compensation factor (TCF) raised to a power equal to the temperature at the time associated with the calibration point (T,cal) minus the temperature at the time associated with the raw analyte signal reading (T,m). Still further by way of example, a lag-compensated glucose value (G-final) may be calculated 240, where this value equals the temperature-compensated glucose value (G-temp), as just described, plus a lag factor (k) multiplied by the change in the temperature-compensated glucose value (ΔG-temp) over a period between two acceptable or consecutive calibration points and divided by the change in time (ΔT) over a period between two acceptable or consecutive calibration points.

The foregoing description provides various calibration or correction algorithms that may be used to convert an analyte concentration obtained from bodily fluid to an analyte concentration obtained from blood. It will be understood that any of a variety of calibration or correction processes or algorithms may be used, such as any suitable means or devices described in any of the above-mentioned U.S. Pat. Nos. 6,175,752, 6,514,718, 6,565,509, and 6,881,551; U.S. Patent Application Publication No. 2003/0187338 filed Apr. 18, 2003, Schmidtke et al., *Measurement and Modeling of the Transient Difference Between Blood and Subcutaneous Glucose Concentrations in the Rat after Injection of Insulin*, Proc. Of the Nat'l Acad. Of Science, 92, pp. 294-299 (1998); and Quinn et al., *Kinetics of Glucose Delivery to Subcutaneous Tissue in Rats Measured with 0.3 mm Amperometric Microsensors*, Am. J. Physiol., 269 (Endocrinol. Metab. 32), E155-E161 (1995). Once an analyte concentration is appropriately calibrated, it may be used as a basis for suitable administration of a suitable amount of a drug, such as insulin, for example, to the patient or subject.

Any of various statistical analyses of the data may follow, such as those exemplified in the Experimental Study described below, for example. By way of example, a Clarke error analysis 242 may be conducted to determine values that may be plotted on a Clarke error grid. Suitable data for such a plot includes analyte concentration values from an implanted analyte sensor and analyte concentration values from venous blood. Further by way of example, root mean square error, average error, slope, intercept, correlation coefficient, and/or the like, may be determined 244. Suitable data for such a determination includes analyte concentration values from an implanted analyte sensor and analyte concentration values from venous blood. Merely by way of example, analyte concentration values from venous blood (YSI) may be measured on a YSI 2300 instrument (Yellow Springs Instruments, Yellow Springs, Ohio), as described in the Experimental Study that follows. Other statistical determinations may be made as desired or useful.

As indicated above, this application is related to, and claims priority based on, the Feldman et al. Application, which is the subject of the Feldman et al. Publication. The Feldman et al. Application and the Feldman et al. Publication described Wired Enzyme™ sensing technology (Abbott Diabetes Care) for the continuous measurement of in vivo glucose concentrations. Such Wired Enzyme™ sensing technology offers excellent sensor stability, reduced sensor susceptibility to variations in in vivo oxygen concentration, and minimized sensor response to common electroactive interferents, as demonstrated in the Experimental Study described below.

Experimental Study

In a sensor-response study, 48 subcutaneous sensors based on Wired Enzyme™ sensing technology were implanted in patients with Type 1 diabetes (25 in the upper arm, and 23 in the abdomen). These implanted sensors were prospectively calibrated using capillary blood. When glucose concentration values from the sensors were compared with those from venous plasma obtained at 15-minute intervals, ninety-eight percent of the values fell in a zone consisting of the clinically accurate Clarke error grid zone A and the clinically acceptable zone B. Neither the site of the implanted sensor (upper arm versus abdomen) nor the site of the capillary blood extraction (arm versus finger) affected system accuracy. The foregoing study and results are further described herein, following the introduction below.

Introduction

Evidence suggests that improved glycemic control can minimize many of the complications associated with Type 1 diabetes. (See, *Diabetes Control and Complications Trial Research Group: The Effect of Intensive Treatment of Diabetes on the Development and Progression of Long-Term Complications in Insulin-Dependent Diabetes Mellitus*, N. Engl. J. Med., 329, pp. 977-986 (1993).) Frequent self-monitoring of blood glucose, in concert with intensive insulin therapy, greatly improves glycemic control.

Continuous glucose sensing provides all of the advantages of high-frequency, discrete testing. It also provides advantages of its own. By way of example, continuous glucose sensing may provide valuable information about the rate and direction of changes in glucose levels, which information may be used predictively or diagnostically. Further by way of example, as continuous glucose sensing occurs at times when discrete testing does not usually occur, such as post-prandially or during sleep, for example, continuous glucose sensing may provide sensitive alarms for hyperglycemia and hypoglycemia that may be associated with post-prandial or resting conditions.

The above-mentioned FreeStyle Navigator® continuous glucose sensor is a subcutaneous, electrochemical sensor, which operates for three days when implanted at a site in the body. This sensor is based on the above-mentioned Wired Enzyme™ sensing technology, a mediated glucose-sensing technology that offers a number of advantages over conventional oxygen-dependent, electrochemical, glucose-sensing technologies, which utilize hydrogen peroxide ($H_2O_2$) detection at high applied potential (~500 mV vs. a silver/silver chloride (Ag/AgCl) reference electrode). (See, Csoregi, E., Schmidtke, D. W., and Heller, A., *Design and Optimization of a Selective Subcutaneously Implantable Glucose Electrode Based on "Wired" Glucose Oxidase*, Anal. Chem., 67, pp. 1240-1244 (1995).)

Wired Enzyme™ technology works at a relatively gentle oxidizing potential of +40 mV, using an osmium (Os)-based mediator molecule specifically designed for low potential operation and stably anchored in a polymeric film for in vivo use. The sensing element is a redox active gel that comprises Os-based mediator molecules, attached by stable bidentate anchors to a polymeric backbone film, and glucose oxidase (GOx) enzyme molecules, permanently coupled together via chemical cross-linking. This redox active gel is a glucose-sensing gel, which accurately transduces glucose concentrations to a measured current over a glucose range of 20-500 mg/dL.

Wired Enzyme™ sensing technology offers three primary advantages over conventional $H_2O_2$-based detection systems, which rely on oxygen for signal generation. One advantage is that this Wired Enzyme™ technology affords electrochemical responses that are extremely stable. This is not the case with many other implanted, or in vivo, glucose sensors, which have been associated with drifts in sensitivity (output per unit glucose concentration) over their lifetimes. (See: Roe, J. N., and Smoller, B. R., *Bloodless Glucose Measurements*, Crit. Rev. Ther. Drug Carrier Syst., 15, pp. 199-241 (1998); and Wisniewsky, N., Moussy, F., and Reichert, W. M., *Characterization of Implantable Biosensor Membrane Biofouling*, Fresenius J. Anal. Chem., 366, pp. 611-621 (2000).) Because of these drifts, many other implanted glucose sensors require frequent and/or retrospective calibration. By contrast, after an initial break-in period, Wired Enzyme™ implanted glucose sensors have extremely stable in vivo sensitivities, typically losing no more than 0.1% sensitivity per hour.

Another advantage is that Wired Enzyme™ technology does not rely on oxygen for signal generation. Although oxygen can compete for electrons with the Os-based mediator molecules, and thereby modestly reduce the sensor output, the overall effect is much smaller than exists in conventional $H_2O_2$-measuring systems, which can generate no signal in the absence of oxygen. This reduced oxygen dependency results in minimal sensitivity to in vivo oxygen variations and good linearity at high glucose concentrations. Yet another advantage is that Wired Enzyme™ implanted glucose sensors operate at an applied potential of only +40 mV, which is much gentler than the ~500 mV required by $H_2O_2$-sensing systems. Oxidation of many interferents (acetaminophen, uric acid, etc.) and subsequent, false, high glucose readings, are minimized at the comparatively low operating potential of +40 mV associated with Wired Enzyme™ sensors.

The Feldman et al. Application presented preliminary results from an accuracy study conducted in 30 patients with Type 1 diabetes, using frequent venous blood glucose measurements (at 15-min intervals, for 3 days), as reference values. The study was performed with a corded system, although use of a wireless system or radio-frequency based system is contemplated according to the present invention. (See: U.S. Pat. Nos. 6,175,752 and 6,565,509 to Say et al. filed on Apr. 30, 1998 and Sep. 21, 2000, respectively; and U.S. Patent Application Publication No. 2004/0186365 A1 of Jin et al. filed on Dec. 26, 2003.) The study and its results are further described below.

Sensor Description

A continuous glucose sensor 300, as schematically shown in FIG. 3, was used in the study described above. This continuous glucose sensor 300 is the FreeStyle Navigator® continuous glucose monitoring device that is based on Wired Enzyme™ technology, as described above. The sensor 300 is an amperometric sensor that comprises three electrodes, a working electrode 302, a reference electrode 304, and a counter electrode 306, contacts of which are shown in FIG. 3. Each of the working electrode 302 and the counter electrode 306 is fabricated from carbon. The reference electrode 304 is an Ag/AgCl electrode. The sensor 300 has a subcutaneous portion 308 having dimensions of about 5 mm in length, 0.6 mm in width, and 0.25 mm in thickness, as further detailed in the enlarged portion of FIG. 3.

The working electrode 302 has an active area 310 of about 0.15 mm This active area 310 is coated with the Wired Enzyme™ sensing layer 312, which is a cross-linked, glucose-transducing gel. As this sensing layer or gel 312 has a relatively hydrophilic interior, glucose molecules surrounding the subcutaneous portion 308 of the sensor 300 are free to diffuse into and within this glucose-transducing gel. The gel 312 is effective in the capture of electrons from these glucose molecules and the transportation of these electrons to the working electrode 302. A schematic illustration of the Wired Enzyme™ sensing layer 312, showing various of its components (as further described below), as well as the path of electron flow in the direction depicted by arrows 314, from the glucose to the working electrode 302, is shown in FIG. 4A.

The sensing layer or gel 312 comprises a redox polymer mediator 316 of high molecular weight, glucose oxidase ("GOx") 318, and a bi-functional, short-chain, epoxide cross-linker (not shown), the former two of which are shown in FIG. 4A. The sensing layer 312 has a mass of 300 ng (at a dry thickness of about 2 μm) and comprises about 35% by weight redox polymer 316, 40% by weight GOx enzyme 318, and 25% by weight cross-linker. The redox polymer 316, the structure of which is illustrated in FIG. 4B, comprises a modified poly(vinylpyridine) backbone, which is loaded with poly(bi-imidizyl) Os complexes that are securely anchored to the backbone via bidentate linkage. (See: U.S. Provisional Patent Application No. 60/165,565 of Mao et al. filed on Nov. 15, 1999; U.S. Pat. No. 6,605,200 of Mao et al. filed on Nov. 14, 2000; U.S. Pat. No. 6,605,201 of Mao et al. filed on Nov. 14, 2000; U.S. Pat. No. 7,090,756 of Mao et al. filed on Aug. 11, 2003; U.S. Pat. No. 6,676,816 of Heller et al. filed on May 9, 2002; and U.S. Pat. No. 7,074,308 of Mao et al. filed on Nov. 14, 2003.) This polymer 316 is an effective mediator or facilitator of electron transport in the sensing layer.

As shown in FIG. 3, the sensor 300 also comprises an analyte-restricting membrane 320, here, a glucose-restricting membrane, disposed over the sensing layer 312. (See: U.S. patent application Ser. No. 10/146,518 filed on May 14, 2002 and issued as U.S. Pat. No. 6,932,894.) The membrane 320 comprises a poly(vinylpyridine)-poly(ethylene glycol) copolymer of high molecular weight, that is cross-linked using a tri-functional, short-chain epoxide. The membrane 320, which is about 50 μm thick, serves to reduce glucose diffusion to the active sensing layer 312 by a factor of about 50. The hydrophilic membrane 320 provides a surface that is biocompatible, such that bodily irritation from the subcutaneous portion 308 of the sensor 300 is reduced.

The sensor 300 is associated with an in vivo sensitivity of about 0.1 nA/(mg/dL) and a linear response over a glucose concentration range 20-500 mg/dL. Additionally, in terms of response to an instantaneous change in glucose concentration, the sensor 300 is associated with a response time of about three minutes.

Sensor Configuration

For each sensor 300 that was used in the study, the subcutaneous portion 308 of the sensor was placed into the subcutaneous tissue of the upper arm or the abdomen of a subject or patient using a spring-actuated insertion mechanism. (See: U.S. Provisional Patent Application No. 60/424,099 of Funderburk et al. filed on Nov. 5, 2002; and U.S. Pat. No. 7,381,184 of Funderburk et al. filed on Nov. 5, 2003.) The sensor 300 was connected via cord (not shown) to a portable, potentiostat-data logger device (not shown), which was used to maintain the glucose-sensing working electrode 302 at a potential of +40 mV versus the Ag/AgCl reference electrode 304, while obtaining and storing instantaneous current values at 10-second intervals. Each subject was also fitted with a small (about 1 $cm^2$), insulated, transdermal skin-temperature sensor, in the immediate vicinity of the continuous glucose sensor 300.

In Vitro Continuous Glucose Sensor Evaluations

In vitro continuous glucose sensor evaluations were carried out at 37° C. in 0.1 M phosphate-buffered saline (PBS) contained in a 2-L jacketed beaker with gentle stirring. Oxygen dependence experiments were conducted under two gas mixtures: 95% $N_2$/5% $O_2$ and 98% $N_2$/2% $O_2$. Interferent evaluations were conducted in separate experiments using 0.2 mM acetaminophen, 0.085 mM ascorbate, or 0.5 mM uric acid, also in PBS. In long-term stability experiments, Proclin 500 (Supelco, Bellefonte, Pa.) was added to the interferent evaluation solution at 5 μL/L to retard bacterial growth.

Biocompatibility Testing

Biocompatibility testing was performed on large-scale assemblies consisting of all sensor components (substrate, electrode inks, membrane, and sensing layer formulations) in proportions corresponding exactly to the actual composition of the continuous glucose sensors 300. (See U.S. Pat. No. 6,175,752 to Say et al.) Cytotoxicity was assessed by ISO elution test (minimum essential medium extract) in vitro.

Sensitization was assessed with a maximization test (Magnusson Kligman method) in guinea pigs. Irritation was assessed with an ISO intra-cutaneous reactivity test in rabbits. Systemic toxicity was assessed by a USP systemic injection test in rabbits. Sub-chronic sensitization was assessed by a 30-day implantation test in rabbits. Genotoxicity was assessed by Ames mutagenicity test in vitro. Hemocompatibility was assessed by a hemolysis test (extract method) in vitro. All tests were passed.

Clinical Trial Procedure

In a clinical trial, thirty subjects were tested, as described below, over a 3-day trial period. Each subject was fitted with either one continuous glucose sensor or two such sensors, and correspondingly, one transdermal skin temperature sensor or two such sensors, as described above. Sensor implant depth was about 5 mm. Each subject was also fitted with a heparin lock for obtaining venous blood samples. Glucose and temperature data were obtained at 10-second intervals over the 3-day trial period, while venous blood samples were obtained at 15-minute intervals over the trial period. Venous plasma blood glucose values were measured on a YSI 2300 (Yellow Springs Instruments, Yellow Springs, Ohio). Capillary blood measurements were also made using the above-mentioned FreeStyle® blood glucose-monitoring system to enable development of a prospective calibration algorithm. Arm capillary blood was obtained hourly at hours 0-12, 24-30, and 48-54, for all of the subjects. Finger capillary blood was also obtained at the same times for 10 subjects wearing 19 continuous glucose sensors.

Glycemic challenges were performed daily for all subjects. Subjects were given intravenous insulin once (0.15 U/kg, followed by 0.10 U/kg if necessary to achieve hypoglycemia), and oral glucose (75 g) on two separate occasions. Vital signs were monitored at 15-minute intervals during administration of intravenous insulin.

An institutional review board approved the trial protocol. Inclusion criteria for the study were the following: presenting Type 1 diabetes, having a C-peptide concentration of less than 0.5 ng/mL, and being 18 years old or older. Thirty subjects were enrolled at three clinical trial sites (Renton, Wash.; San Antonio, Tex.; and Walnut Creek, Calif.). Subjects ranged in age from 20 to 85 years, with a mean of 40 years. There were eight females and 22 males, comprising three African Americans, 26 Caucasians, and one Hispanic.

Calibration Procedure

A prospective calibration algorithm was developed in an earlier study consisting of 20 sensors (15 arm, 5 abdominal) implanted into subjects with Type 1 diabetes. The 48 sensors, whose performance is described here, were implanted in a separate study conducted sequentially following the calibration development set. Therefore, none of the data sets described in the present study was used in development of the calibration algorithm. For each implant, three capillary blood glucose measurements, obtained using the FreeStyle® blood glucose-monitoring system, were used as calibration bases, subject to exclusion criteria based on time, glucose concentration range, rate of glucose concentration change, sensitivity, and temperature, as further described below.

As to time, calibration point 1 occurred a minimum of 1 hour after insertion, calibration point 2 occurred a minimum of 2 hours after a successful calibration point 1, and calibration point 3 occurred a minimum of 21 hours after a successful calibration point 2. As to glucose concentration range, calibration was allowed within a capillary blood glucose concentration range of 60-350 mg/dL. As to rate of glucose concentration change, calibration was restricted to rates of change of 2 (mg/dL)/min or less. (A separate study in 20 patients with Type 1 diabetes performing normal daily routines (i.e., not performing daily glucose challenges) showed that the rate of 2 (mg/dL)/min was exceeded only 4% of the time, consistent with other published data. See Jungheim, K., Kapitza, C., Djurhuus, C. B., Wientjes, K. J., and Koschinsky, T., *How Rapid Does Glucose Concentration Change in Daily-Life of Patients with Type* 1 *Diabetes?*, Abstract, Presented at the Second Annual Diabetes Technology Meeting, Diabetes Technology Society, Atlanta, Ga. (November 2002).) As to sensitivity, calibration was allowed only if the resulting nominal sensitivity (in nA/mM glucose) was within a preset range as determined by a code assigned to each continuous glucose sensor production lot. As to temperature, calibration was allowed over a skin temperature range of 28-37° C.

The operating sensitivity for the first 2 hours of operation was based entirely on calibration point 1. However, subsequent operating sensitivities (after the second calibration point was obtained) were based on a weighted average of all previously obtained calibration points. This had the effect of refining, and increasing the accuracy of, the calibration as the implant proceeded. This refinement process was made possible by the near-negligible drift of the continuous glucose sensor sensitivity with time.

The calibration process also involved a correction for changes in skin temperature underneath the insulated skin temperature probe. An adjustment of 7% per ° C., relative to the skin temperature at the time of the operative calibration point, was performed. One sensor (of 49 implanted) did not achieve calibration, because of violation of the sensitivity restriction described above. That sensor was excluded from the statistical analysis.

Results

The continuous glucose sensor was found to have excellent in vitro stability. This was demonstrated by a plot that showed the responses (current, in nA) of three separate sensors in glucose at 500 mg/dL (in PBS, at 37° C.) versus time (days) over a period of 7 days, as shown in the Feldman et al. Application and Feldman et al. Publication (see FIG. 3). The average total decay in glucose signal over the 7-day test period was 1.7%. The mean hourly rate of decay, at 0.011% per hour, is insignificant. Similar stabilities have been observed in vivo (vide infra).

In vitro testing was also performed to determine the effect of oxygen on the linearity of the continuous glucose sensors. This results were displayed in a plot of the averaged response (current, in nA) versus glucose concentration (mg/dL) of eight continuous glucose sensors that were maintained under an oxygen tension of 15 torr, and a plot of the same, but with the sensors maintained under an oxygen tension of 38 torr, as shown in the Feldman et al. Application and Feldman et al. Publication (see FIG. 4). (The lowered $O_2$ levels reflect the reduced levels found in subcutaneous tissue. See Burtis, C. A., and Ashwood, E. R., eds., *Tietz Textbook of Clinical Chemistry*, W.B. Saunders Co., Philadelphia, Pa. (1999).) Curves drawn for the two plots exhibit excellent linearity ($R^2$=0.9999 for both curves) over the glucose range of from 18 to 540 mg/dL. The curves differ in slope by only 4%, with differences varying from 0.4% at 36 mg/dL to 3.5% at 540 mg/dL. These results indicate that the continuous glucose sensors are only minimally oxygen dependent.

In vitro testing was performed to determine the effect of three interferents, namely, acetaminophen, ascorbate, and uric acid, at the top of their normal physiological or therapeutic range (0.2 mM, 0.085 mM, and 0.5 mM, respectively (see Burtis, C. A., and Ashwood, E. R., eds., *Tietz Textbook of Clinical Chemistry*, W.B. Saunders Co., Philadelphia, Pa.

(1999)), on continuous glucose sensors. The glucose-equivalent interferences were 3 mg/dL for acetaminophen, 19 mg/dL for ascorbate, and 3 mg/dL for uric acid, tested at these levels. The interferences due to uric acid and acetaminophen are inconsequential, which can be attributed largely to the low operating potential (+40 mV versus Ag/AgCl) associated with the continuous glucose sensors.

In vivo testing of continuous glucose sensors, as implanted, was performed. Representative results of the testing are shown in FIG. 5, in the form of an overlay plot of representative data from an abdominally implanted continuous glucose sensor (current (in nA) versus time (in days)) and venous plasma glucose values (glucose concentration (in mg/dL) versus time (in days)). It should be noted that the data were raw, that is, not calibrated and not corrected for temperature, and no time-shifting of the data was performed.

The results are noteworthy in that they demonstrate what is obviously an excellent correlation between the raw current values associated with the continuous glucose sensor and the venous plasma glucose concentrations. No substantial lag between subcutaneous and venous glucose concentrations is evident. The results are also noteworthy in that they demonstrate that the sensitivity of the implanted continuous glucose sensor is essentially unchanged over the 3-day implantation period. Given this stability in signal sensitivity, it is possible to schedule three calibration points in the first 24 hours of the implantation, with no additional calibration points during the final 48 hours. Additionally, given nearly negligible sensor drift, it is possible to use a weighted average of multiple calibration points as a basis for accounting for the operating sensitivity of the implanted sensor. Such use of a weighted average is helpful reducing any error inherent in the capillary blood glucose measurement that is used for calibration.

In vivo testing of continuous glucose sensors, as implanted in the arms of the subjects, was performed. Representative results of the testing are shown in FIG. 6 in the form of a plot (glucose concentration (in mg/dL) versus time (in days)) of representative data from an arm-implanted continuous glucose sensor (one of the 48 calibrated sensors), venous plasma, and capillary blood from an arm-stick. It should be noted that the current data obtained from the arm-implanted continuous glucose sensor was converted to glucose concentration data, by way of a prospective calibration that was based on the arm-capillary blood measurements that were obtained using the FreeStyle® blood glucose-monitoring system. No time-shifting of the data was performed.

The results are noteworthy in that they demonstrate an excellent correlation between subcutaneous and venous plasma glucose values, which is indicative of both reliable sensor function and accurate calibration. As noted above, the representative data set shown in FIG. 6 was calibrated using arm-capillary blood measurements. The results are also noteworthy in that no significant change in accuracy was found (vide infra) when the data were calibrated using finger-capillary blood measurements.

In vivo testing of continuous glucose sensors, as simultaneously implanted in the arm and in the abdomen of a single subject, was performed. Representative results of the testing are shown in FIG. 7, in the form of a plot (glucose concentration (in mg/dL) versus time (in days)) of representative data from an arm-implanted continuous glucose sensor, an abdomen-implanted continuous glucose sensor, and venous plasma. The results demonstrate good agreement between the glucose values measured at subcutaneous sites in the arm and in the abdomen.

These results also demonstrate good agreement between the subcutaneous glucose values associated with the arm and abdomen and those associated with the venous plasma, although some deviations from the latter were observed on the first night of implantation, when the subcutaneous values fell intermittently below the venous plasma values. Based on data (not shown) for spatially adjacent sensors implanted at a single site, it is believed that these deviations result from interactions between the sensor and the insertion site, not from systematic differences between venous and subcutaneous glucose in the body. The deviations are virtually always negative (that is, the glucose value from the implanted continuous glucose sensor is lower than the glucose value from the venous plasma) and tend to occur at night and early in the course of the 3-day implantation.

The cause of the negative deviations described above is unknown, although some possible causes may be put forward, as follows. It may be that cells or other subcutaneous structures adhere to the sensor surface, blocking glucose ingress. It may be that blood clots form upon sensor insertion, exerting a similar glucose-blocking effect. (Blood clots were not observed to adhere to the active areas of explanted sensors (that is, sensors that were removed from the body after implantation), but that does not preclude their presence prior to explantation.) It may be that constriction of local blood vessels, due to external pressure effects, restrict glucose delivery to the sensor site.

It should be noted that the deviations described above are not frequent. Sensitivity was reduced by 40% or more for only 4% of the roughly 3,500 sensor-hours represented by this study. Overall, the system performed well, as demonstrated by statistical data described below.

A Clarke error grid of data (glucose concentration from the continuous glucose sensor versus that in venous plasma (mg/dL)) from all of the 48 continuous glucose sensors (25 in the arm and 23 in the abdomen) that were inserted in the 30 subjects, is shown in FIG. 8. These data were prospectively calibrated, with no time-shifting, using arm-capillary blood data. The grid represents 12,667 data pairs. Approximately 98% of the data fall within a zone consisting of the clinically accurate "A" region and the clinically acceptable "B" region of the Clarke error grid.

A tabular summary of statistical data from the Clarke error grid and from the implanted continuous glucose sensors is presented in Table 1 below. In Table 1, the data are categorized according to the implantation site, either arm or abdomen, and/or the calibration site, either arm or finger.

TABLE 1

Summary of Statistical Data

| Subset | Description | Calibration Site | $N^a$ | % A | % B | % C | % D | % E | ARE (%) |
|---|---|---|---|---|---|---|---|---|---|
| A | All sensors (25 arm, 23 abdominal) | Arm | 12,667 | 67.9 | 29.7 | 1.2 | 1.1 | 0.0 | 17.3 |

TABLE 1-continued

Summary of Statistical Data

| Subset | Description | Calibration Site | N[a] | Clarke error grid | | | | | ARE (%) |
| --- | --- | --- | --- | --- | --- | --- | --- | --- | --- |
| | | | | % A | % B | % C | % D | % E | |
| B | 25 sensors (arm) | Arm | 6,656 | 67.0 | 30.3 | 1.8 | 1.0 | 0.0 | 17.7 |
| C | 23 sensors (abdominal) | Arm | 6,011 | 69.0 | 29.1 | 0.6 | 1.3 | 0.0 | 17.2 |
| D[b] | 19 sensors (arm, finger calibration available) | Arm | 4,987 | 67.7 | 29.3 | 1.8 | 1.1 | 0.0 | 17.4 |
| E[b] | 19 sensors (arm, finger calibration available) | Finger | 4,922 | 68.2 | 29.8 | 1.1 | 0.8 | 0.0 | 17.0 |

[a]Number of continuous sensor/venous plasma data pairs.
[b]Subsets D and E have slightly different n values, since there were small variations in the time at which calibrated operation (and hence meaningful venous/subcutaneous glucose pairs) began.

More particularly, the data described above in relation to FIG. 8 appears in Table 1 in association with a Subset A, representing arm-based calibration, for the data from the 48 continuous glucose sensors (25 in the arm and 23 in the abdomen). This data is further broken down in Table 1 for the 25 sensors that were implanted in the arm (Subset B) and the 23 sensors that were implanted in the abdomen (Subset C). The data demonstrates that when arm-capillary blood calibration was employed, there was no significant difference between the use of an insertion site in the arm, associated with an absolute relative error ("ARE") of 17.7% (for 25 sensors, Subset B), and use of an insertion site in the abdomen, associated with an ARE of 17.2% (for 23 sensors, Subset C).

The other data appearing in Table 1 were obtained from 19 sensors that were used to simultaneously determine glucose values using calibration samples withdrawn from both the arm (Subset D) and the finger (Subset E) of a subject on an hourly basis for hours 0-12, 24-30, and 48-54. The data were obtained in this manner from 10 subjects. The data show that of 4,987 continuous sensor/venous plasma data pairs in Subset D, representing arm-based calibration, 67.7% were found to be in region A of the Clarke error grid, 29.3% in region B, 1.8% in region C, 1.1% in region D, and 0.0% in region E. The data further show that of the 4,922 continuous sensor/venous plasma data pairs in Subset E, representing finger-based calibration, 68.2% were found to be in region A of the Clarke error grid, 29.8% in region B, 1.1% in region C, 0.8% in region D, and 0.0% in region E. The data in Table 1 demonstrate that there is no significant difference between arm-capillary blood calibration (ARE=17.4%) and finger-capillary blood calibration (ARE=17.0%). Accordingly, arm-capillary blood may be used more or less as effectively as finger-capillary blood as the basis for one-point in vivo calibration.

Conclusions

All of the continuous glucose sensor data presented above (with the exception of the raw data overlay of FIG. 5) were derived using a prospective calibration based on nominal calibration times of 1, 3, and 24 hours after implantation. The calibration algorithm was developed using a separate data set for 20 similar implanted continuous glucose sensors. None of the data reported here was used in development of the calibration algorithm.

As demonstrated herein, the continuous glucose sensor used in the study is extremely stable in terms of in vivo sensitivity after a modest acclimation process (during which sensitivity may rise by a few percent) that is generally complete in a few hours. Because sensor output is so stable, calibration points may be concentrated in the first 24 hours of use and calibration may be periodically or continuously refined as multiple calibration points are obtained. Both of these strategies may be advantageous for a number of reasons. By way of example, the concentration of calibration points in an early portion of the implantation period, such as the first 24 hours, for example, may be advantageous in that no calibration is required over the remaining portion of the implantation period, such as the final 48 hours of a 72-hour period of implantation, for example. Further by way of example, either this concentration of calibration points early on, or the above-described refinement of the calibration, as opposed to the use of the most recent calibration point as a basis for calibrating the sensor, or both, may be advantageous in the reduction or minimization of calibration error.

It is noteworthy that no time-shifting of data was used in the study described herein. That is, all of the data are real-time data. Time-shifting of data has been used frequently in the literature to compensate for any error associated with physiological time lags between the subcutaneous and reference glucose measurements or associated with slow system response times. As it is believed that time-shifting of glucose values and prospective calibration are incompatible concepts, time-shifting of data, such as glucose values, may be avoided according to the present invention.

Based on the statistical data provided herein, the average physiological time lag (subcutaneous-venous) associated with the continuous glucose sensors tested was found to be about 8 minutes. This value was determined by the theoretical exercise of finding the minimum in absolute relative error as reference and subcutaneous values were time-shifted. Of this 8-minute lag, about 3 minutes and 5 minutes can be attributed to the response time of the sensor, and to physiology, respectively. In a recent review (see Roe, J. N., and Smoller, B. R., *Bloodless Glucose Measurements*, Crit. Rev. Ther. Drug Carrier Syst., 15, pp. 199-241 (1998)) of various subcutaneous glucose measurement strategies, lag times ranging from 2 to 30 min, with an average lag of 8-10 minutes, were reported, which is in good agreement with the findings of this Experimental Study. A more complete study of physiological glucose lags based on the raw data of this study has been presented at the 39th Annual Meeting of the German Diabetes Association, in Hannover, Germany, May 19 to May 22, 2004, by Feldmen, B., and Sharp, C., under the title, *Correlation of Glucose Concentrations in Intersitital Fluid and Venous Blood during Periods of Rapid Glucose Change*.

The data for the continuous glucose sensor tested, as shown in FIGS. 5-7, demonstrate excellent linearity at both high and low glucose values induced by glycemic challenges. The continuous glucose sensor faithfully tracks in vivo glucose values over the physiologically relevant range. Overall, for the complete data set, 98% of readings fall within a zone that consists of the clinically accurate Clarke error grid zone A and the clinically acceptable zone B, as shown in FIG. 8 and Table 1. This represents excellent performance. It should be noted that no only does the continuous glucose sensor perform outstandingly, it provides directional trend information, a very desirable predictive or diagnostic tool.

The data summarized in Table 1 demonstrates that there was no significant difference between arm-capillary blood calibration, associated with an ARE of 17.4%, and finger-capillary blood calibration, associated with an ARE of 17.0%. Thus, arm-capillary blood served as an almost equally accurate, and less painful, calibration tool, relative to finger-capillary blood. While not studied here, it is contemplated that rubbing of skin adjacent to a calibration site (see the FreeStyle® Blood Glucose Testing System, Test Strip Package Insert, TheraSense, Inc., Alameda, Calif. (2000)), such as a calibration site in the arm, may improve the efficacy of the capillary blood from that site as a calibration tool. The data summarized in Table 1 also demonstrates that when arm-capillary blood calibration was employed, there was no significant difference between the use of an insertion site in the arm, associated with a ARE of 17.7% (for 25 sensors), and use of an insertion site in the abdomen, associated with a ARE of 17.2% (for 23 sensors).

The possibility of a large variation between arm- and finger-capillary blood values has been put forth in various studies conducted under the extreme conditions of glucose loading, followed by intravenous delivery of insulin. (See Koschinsky, T., and Jungheim, K., *Risk Detection Delay of Fast Glucose Changes by Glucose Monitoring at the Arm*, Diabetes Care, 24, pp. 1303-1304 (2001).) In fact, under normal use conditions, these differences are not significant unless glucose is changing very rapidly. (See Bennion, N., Christensen, N. K., and McGarraugh, G., *Alternate Site Glucose Testing: A Crossover Design*, Diabetes Technol. Ther., 4, pp. 25-33 (2002).) Restriction of calibration to rates of less than 2 mg/dL per min virtually eliminates this possible source of error.

The present invention is applicable to corded or cabled glucose-sensing systems, as described above, as well as other analyte-sensing or glucose-sensing systems. For example, it is contemplated that suitable results, along the lines of those described herein, may be obtained using a wireless glucose-sensing system that comprises a pager-sized, hand-held, informational display module, such as a FreeStyle Navigator® wireless glucose-sensing system. The FreeStyle Navigator® system employed herein is capable of providing real-time glucose information at 1-minute intervals and information regarding rates and trends associated with changes in glucose levels. This system is further capable of providing a visual indication of glucose level rates, allowing users to discriminate among glucose rate changes of less than 1 mg/dL per minute, 1-2 mg/dL per minute (moderate change), and greater than 2 mg/dL per minute (rapid change). It is contemplated that sensors having features such as these will be advantageous in bringing information of predictive or diagnostic utility to users. The FreeStyle Navigator® system is also designed to provide hypoglycemic and hyperglycemic alarms with user-settable thresholds.

Each of the various references, presentations, publications, provisional and/or non-provisional United States patent applications, United States patents, non-U.S. patent applications, and/or non-U.S. patents that have been identified herein, is incorporated herein in its entirety by this reference.

Other aspects, advantages, and modifications within the scope of the invention will be apparent to those skilled in the art to which the invention pertains. Various modifications, processes, as well as numerous structures to which the present invention may be applicable will be readily apparent to those of skill in the art to which the present invention is directed upon review of the specification. Various aspects and features of the present invention may have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although various aspects and features of the present invention may have been described largely with respect to applications, or more specifically, medical applications, involving diabetic humans, it will be understood that such aspects and features also relate to any of a variety of applications involving non-diabetic humans and any and all other animals. Further, although various aspects and features of the present invention may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present invention have been described with respect to various embodiments and specific examples herein, all of which may be made or carried out conventionally, it will be understood that the invention is entitled to protection within the full scope of the appended claims.

What is claimed is:

1. An in vivo analyte sensor calibration system, comprising:
   an in vivo analyte sensor, at least a portion of the sensor subcutaneously positioned to generate one or more signals;
   a transmission element operatively coupled to the in vivo analyte sensor and configured to transmit one or more analyte-related signals of the in vivo analyte sensor;
   a calibration sensor configured to be placed in contact with one or more blood samples from one or more off-finger calibration sites to provide one or more calibration measurements; and
   a data processing element configured to physically couple with the calibration sensor to communicate with the transmission element, the data processing element further configured to determine a quality of the one or more calibration measurements and a quality of the one or more generated signals from the in vivo analyte sensor, to convert the one or more generated signals from the in vivo analyte sensor into a corresponding one or more analyte concentration values based on the one or more calibration measurements if the quality of the one or more calibration measurements and the quality of the one or more generated signals from the in vivo analyte sensor are suitable for calibration, to determine an unweighted sensitivity associated with each of the one or more calibration measurements, to determine an adjusted sensitivity weighting factor associated with each of the one or more calibration measurements by multiplying a raw weighting factor by the corresponding unweighted sensitivity for each of the one or more calibration measurements and then further multiplying by a summation of each of the unweighted sensitivities raised to a power of the sensitivity weighting factor, and to determine a weighted sensitivity for each of the one or more calibration measurements based on the adjusted sensitivity factor associated with each of the one or more calibration measurements.

2. The system of claim 1, wherein the in vivo analyte sensor is a glucose sensor.

3. The system of claim 2, wherein the in vivo glucose sensor comprises a sensing element that comprises a glucose responsive enzyme.

4. The system of claim 3, wherein the sensing element comprises a hydrophilic portion.

5. The system of claim 1, wherein the data processing element comprises a hand-held display module.

6. The system of claim 1, wherein the data processing element is configured to evaluate whether the one or more calibration measurements are within a predetermined range of analyte concentration to determine the quality of the one or more calibration measurements.

7. The system of claim 6, wherein the predetermined range comprises about 60 mg/dL to about 350 mg/dL.

8. The system of claim 1, wherein the quality of the generated one or more signals from the in vivo analyte sensor comprises evaluating whether the one or more signals is within a predetermined rate of change of the one or more signals from the in vivo analyte sensor.

9. The system of claim 1, wherein the calibration sensor is an in vitro sensor.

10. The system of claim 1, wherein the calibration sensor is an in vivo calibration sensor.

11. The system of claim 1, wherein the in vivo analyte sensor is a transcutaneous sensor.

12. The system of claim 1, wherein the sensitivity is determined by taking the average of each of the one or more generated signals divided by a corresponding calibration measurement.

13. The system of claim 1, wherein the calibration device is configured to determine a temperature compensated analyte concentration value based at least in part on the one or more analyte concentration values and a temperature compensation factor.

14. The system of claim 13, wherein the calibration device is further configured to determine a lag compensated analyte concentration value by applying a lag factor to a change in the temperature compensated analyte value over a time period between two acceptable calibration points divided by the time period between the two acceptable calibration points added to the temperature compensated analyte value.

15. The system of claim 14, wherein the two acceptable calibration points are deemed acceptable based on at least one evaluation standard being met.

16. The system of claim 1, wherein the data processing unit is further configured to determine a temperature compensated glucose concentration by dividing at least one value of the one or more signals by the corresponding weighted sensitivity value and multiplying by a temperature compensation factor that is raised to a power equal to the difference in the temperature at a time associated with a calibration measurement and the temperature at the time associated with the generated one or more signals.

17. The system of claim 1, wherein the one or more processors is configured to evaluate that a temperature measurement is within a predetermined range of temperatures when determining the quality of the one or more calibration measurements.

18. The system of claim 1, wherein the one or more processors is configured to evaluate a quality of the calibration measurement by comparing the determined weighted sensitivity of the in vivo analyte sensor to a predetermined range.

19. The system of claim 13, wherein the one or more processors is configured to determine a lag corrected glucose concentration value by adding to the determined temperature compensated glucose concentration value a lag correction factor that is multiplied by a change in the temperature compensated glucose concentration value divided by a time period between two calibration measurements minus the temperature divided by the change in time between the two calibration measurements.

20. The system of claim 1, wherein determining the weighted sensitivity for each of the one or more calibration points includes dividing a summation of each of the adjusted sensitivity weighting factors each raised to a power equal to the corresponding unweighted sensitivity by a summation of each of the adjusted sensitivity weighting factors divided by a corresponding sensitivity offset factor.

* * * * *